United States Patent
Forsell

(10) Patent No.: US 9,993,342 B2
(45) Date of Patent: Jun. 12, 2018

(54) HIP JOINT DEVICE AND METHOD

(71) Applicant: Peter Forsell, Bouveret (CH)

(72) Inventor: Peter Forsell, Bouveret (CH)

( * ) Notice: Subject to any disclaimer, the term of this patent is extended or adjusted under 35 U.S.C. 154(b) by 0 days. days.

(21) Appl. No.: 14/857,860

(22) Filed: Sep. 18, 2015

(65) Prior Publication Data
US 2016/0008135 A1 Jan. 14, 2016

Related U.S. Application Data

(63) Continuation of application No. 13/383,300, filed as application No. PCT/SE2010/050831 on Jul. 12, 2010, now Pat. No. 9,138,320.
(Continued)

(30) Foreign Application Priority Data

| Jul. 10, 2009 | (SE) | 0900957 |
|---|---|---|
| Jul. 10, 2009 | (SE) | 0900958 |
| Jul. 10, 2009 | (SE) | 0900959 |
| Jul. 10, 2009 | (SE) | 0900960 |
| Jul. 10, 2009 | (SE) | 0900962 |
| Jul. 10, 2009 | (SE) | 0900963 |
| Jul. 10, 2009 | (SE) | 0900965 |
| Jul. 10, 2009 | (SE) | 0900966 |
| Jul. 10, 2009 | (SE) | 0900968 |
| Jul. 10, 2009 | (SE) | 0900969 |
| Jul. 10, 2009 | (SE) | 0900970 |
| Jul. 10, 2009 | (SE) | 0900972 |
| Jul. 10, 2009 | (SE) | 0900973 |
| Jul. 10, 2009 | (SE) | 0900974 |
| Jul. 10, 2009 | (SE) | 0900976 |

(Continued)

(51) Int. Cl.
*A61F 2/32* (2006.01)
*A61F 2/34* (2006.01)

(52) U.S. Cl.
CPC ........ *A61F 2/34* (2013.01); *A61F 2002/3241* (2013.01); *A61F 2002/343* (2013.01);
(Continued)

(58) Field of Classification Search
CPC ...... A61F 2/32; A61F 2/34; A61F 2/36; A61F 2/36; A61F 2/3603; A61F 2002/4677;
(Continued)

(56) References Cited

U.S. PATENT DOCUMENTS

| 4,159,544 A * | 7/1979 | Termanini | A61F 2/32 623/22.14 |
| 4,718,911 A * | 1/1988 | Kenna | A61F 2/34 623/22.29 |

* cited by examiner

*Primary Examiner* — Brian Dukert

(57) ABSTRACT

A medical device for implantation in a hip joint of a patient is provided. The medical device is adapted to be fixated to the pelvic bone of the patient. The medical device comprises an inner and an outer surface, a contacting portion of the inner surface is spherical and adapted to face the center of the hip joint when said medical device is implanted, and said medical device is adapted to receive a caput femur or a prosthetic caput femur having a spherical portion. The medical device comprises at least one extending portion adapted to clasp the caput femur, or prosthetic caput femur, for restraining said caput femur, or prosthetic caput femur in said medical device. The medical device is adapted to release the caput femur or prosthetic caput femur from the medical device when a predetermined strain is placed on the medical device.

12 Claims, 27 Drawing Sheets

Related U.S. Application Data

(60) Provisional application No. 61/229,738, filed on Jul. 30, 2009, provisional application No. 61/229,739, filed on Jul. 30, 2009, provisional application No. 61/229,743, filed on Jul. 30, 2009, provisional application No. 61/229,745, filed on Jul. 30, 2009, provisional application No. 61/229,746, filed on Jul. 30, 2009, provisional application No. 61/229,747, filed on Jul. 30, 2009, provisional application No. 61/229,748, filed on Jul. 30, 2009, provisional application No. 61/229,751, filed on Jul. 30, 2009, provisional application No. 61/229,752, filed on Jul. 30, 2009, provisional application No. 61/229,755, filed on Jul. 30, 2009, provisional application No. 61/229,761, filed on Jul. 30, 2009, provisional application No. 61/229,767, filed on Jul. 30, 2009, provisional application No. 61/229,778, filed on Jul. 30, 2009, provisional application No. 61/229,786, filed on Jul. 30, 2009, provisional application No. 61/229,789, filed on Jul. 30, 2009, provisional application No. 61/229,796, filed on Jul. 30, 2009, provisional application No. 61/229,735, filed on Jul. 30, 2009.

(30) Foreign Application Priority Data

Jul. 10, 2009 (SE) .......................................... 0900978
Jul. 10, 2009 (SE) .......................................... 0900981

(52) U.S. Cl.
CPC .................. *A61F 2002/3429* (2013.01); *A61F 2002/3475* (2013.01); *A61F 2002/3477* (2013.01); *A61F 2002/3485* (2013.01)

(58) Field of Classification Search
CPC ............ A61B 17/1664; A61B 17/1666; A61B 17/1668; A61B 17/74
See application file for complete search history.

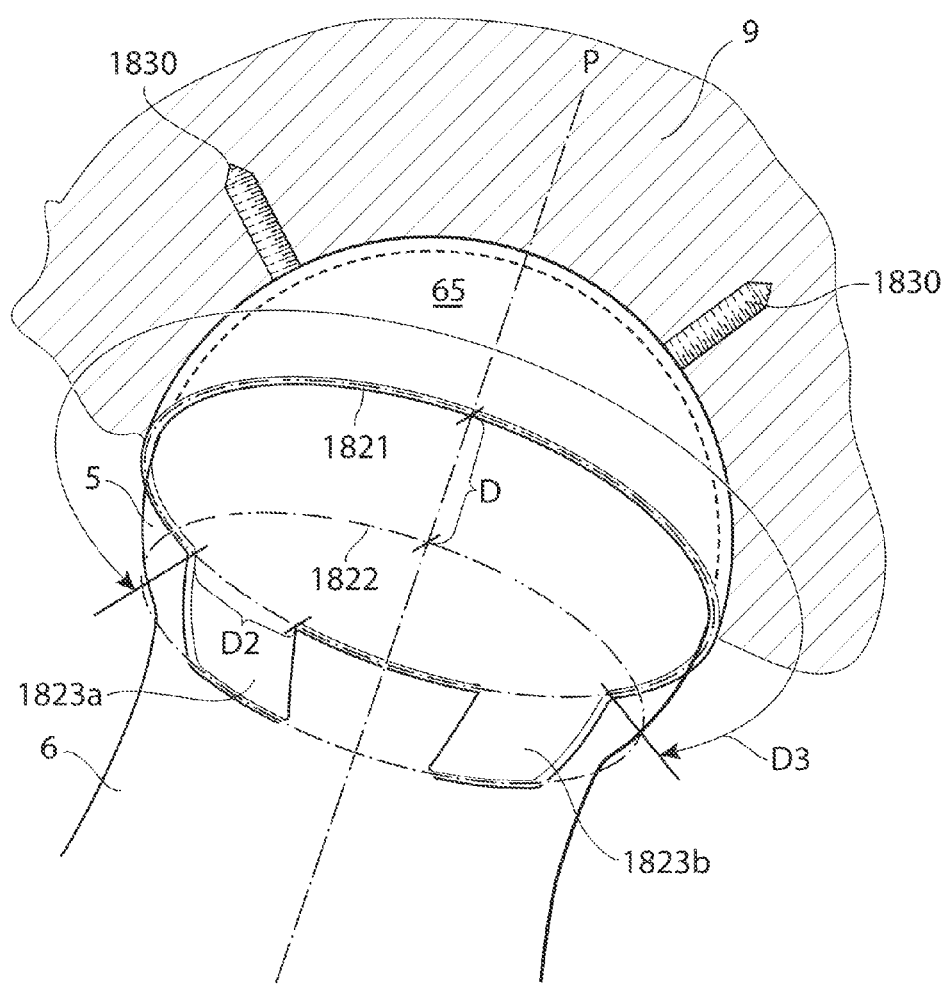

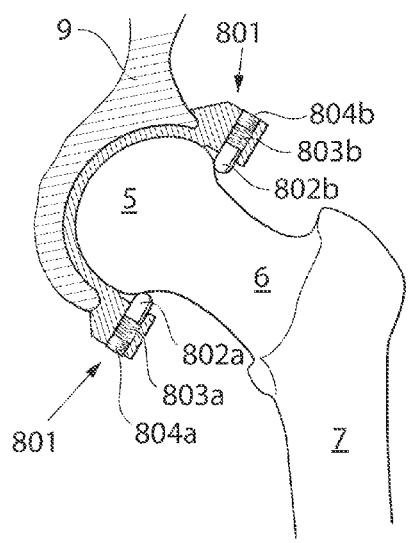
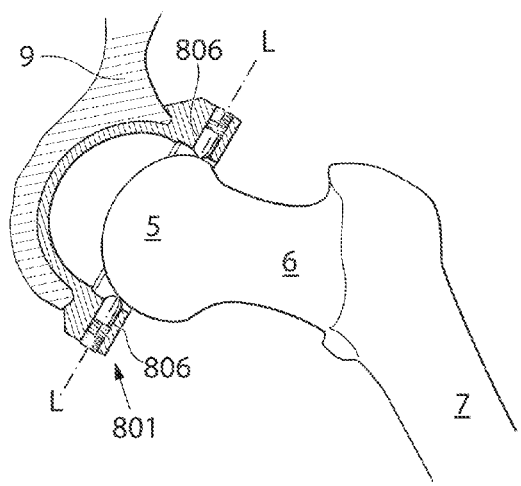
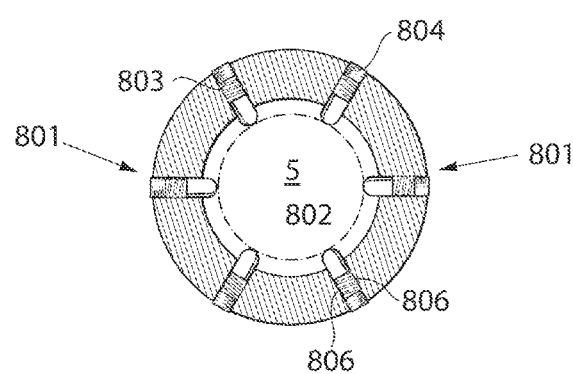

HIP JOINT DEVICE AND METHOD

This application is the continuation of U.S. non-provisional application Ser. No. 13/383,300 filed Jan. 10, 2012 which is the U.S. national phase of International Application No. PCT/SE2010/050831, filed 12 Jul. 2010, which designated the U.S. and claims the benefit of U.S. Provisional No. 61/229,755, filed 30 Jul. 2009; 61/229,738 filed 30 Jul. 2009, 61/229,739 filed 30 Jul. 2009; 61/229,743 filed 30 Jul. 2009; 61/229,745 filed 30 Jul. 2009; 61/229,746 filed 30 Jul. 2009; 61/229,747 filed 30 Jul. 2009; 61/229,748 filed 30 Jul. 2009; 61/229,751 filed 30 Jul. 2009; 61/229,752 filed 30 Jul. 2009; 61/229,761 filed 30 Jul. 2009; 61/229,767 filed 30 Jul. 2009; 61/229,778 filed 30 Jul. 2009; 61/229,786 filed 30 Jul. 2009; 61/229,789 filed 30 Jul. 2009; 61/229,796 filed 30 Jul. 2009; 61/229,735 filed 30 Jul. 2009; and which claims priority to Swedish Application Nos.: 0900981-2 filed 10 Jul. 2009; 0900957-2 filed 10 Jul. 2009; 0900958-0 filed 10 Jul. 2009; 0900959-8 filed 10 Jul. 2009; 0900960-6 filed 10 Jul. 2009; 0900962-2 filed 10 Jul. 2009; 0900963-0 filed 10 Jul. 2009; 0900965-5 filed 10 Jul. 2009; 0900966-3 filed 10 Jul. 2009; 0900968-9 filed 10 Jul. 2009; 0900969-7 filed 10 Jul. 2009; 0900970-5 filed 10 Jul. 2009; 0900972-1 filed 10 Jul. 2009; 0900973-9 filed 10 Jul. 2009; 090097 4-7 filed 10 Jul. 2009; 0900976-2 filed 10 Jul. 2009 and 0900978-8 filed 10 Jul. 2009, the entire contents of each of which are hereby incorporated by reference.

TECHNICAL FIELD

The present invention relates generally to medical devices for implantation in a hip joint.

BACKGROUND ART

The hip joint is a synovial joint, joining the pelvis to the proximal portion of the femoral bone. Synovial joints are the most common types of joints in mammals, and are typical of nearly all limb joints. The contacting surfaces of said the pelvic, the acetabulum, and the contacting surface of the femoral bone, the caput femur, are smooth and rounded, and covered by articular cartilage. A synovial membrane, encapsulates the joint, forming a hip joint cavity, which contains synovial fluid. Outside the synovial membrane is a fibrous capsule and ligaments, forming an articular capsule.

There are both natural and pathological processes leading to deteriorated joint function. With age and wear, the articular cartilage becomes less effective as a shock absorber and a lubricated surface. Different degenerative joint diseases, such as arthritis, osteoartrithis, or osteoarthrosis, accelerate the deterioration.

Hip joint Osteoarthritis is a syndrome in which low-grade inflammation results in pain in the hip joints, caused by abnormal wearing of the Cartilage that acts as a cushion inside if the hip joint. This abnormal wearing of the cartilage also results in a decrease of the joints lubricating fluid called Synovial fluid. Hip joint Osteoarthritis is estimated to affect 80% of all people over 65 years of age, in more or less serious forms.

The present treatment for hip osteoarthritis comprises NSAID drugs, local injections of Hyaluronic acid or Glucocorticoid to help lubricating the hip joint, and replacing parts of the hip joint with a prosthesis through hip joint surgery.

The replacing of parts of the hip joint is one of the most common surgeries to date performed at hundreds of thousands of patients in the world every year. The most common method comprises placing a metal prosthesis in Femur and a plastic bowl in Acetabulum. This operation is done through an incision in the hip and upper thigh and through Fascia Lata and the lateral muscles of the thigh. To get access to the joint, the supporting Capsule attached to Femur and Ilium needs to be penetrated, making it difficult to get a fully functional joint after the surgery. Femur is then cut at the neck with a bone saw and the prosthesis is placed in femur either with bone cement or without. Acetabulum is slightly enlarged using an Acetabular reamer, and the plastic bowl is positioned using screws or bone cement.

The complications after hip joint surgery includes dislocation of the hip joint and loosening of the prosthesis from its fixation in the femoral bone. The loosening and/or dislocation of the prosthesis could be induced by an abnormal strain being placed on the hip joint from e.g. the patient falling or making a rapid movement of the hip, or by a bodily macrophage reaction.

SUMMARY

A medical device for implantation in a hip joint of a patient is provided. The medical device is adapted to be fixated to the pelvic bone of the patient. The medical device comprises an inner and an outer surface, a contacting portion of the inner surface is spherical and adapted to face the center of the hip joint when said medical device is implanted, and said medical device is adapted to receive a caput femur or a prosthetic caput femur having a spherical portion. The medical device comprises at least one extending portion adapted to clasp the caput femur, or prosthetic caput femur, for restraining said caput femur, or prosthetic caput femur in said medical device. The medical device is adapted to release the caput femur or prosthetic caput femur from the medical device when a predetermined strain is placed on the medical device. The ability of the medical device to release the caput femur or prosthetic caput femur from the medical device when a predetermined strain is placed on the medical device reduces the risk that the prosthesis is loosened by an abnormal strain being placed on the hip joint from e.g. the patient falling or making a rapid movement of the hip.

According to another embodiment, the medical device is adapted to receive a caput femur or an artificial replacement therefor, having a collum femur or artificial collum femur fixated to said spherical portion of said caput femur or artificial replacement therefor. The inner surface comprises an equator line, being the largest circular circumference of said inner surface. The at least one extending portion passes beyond said equator line, such that the end portion of said contacting portion of said inner surface forms a circular extension line having a smaller circumference than said equator line. The at least one extending portion longitudinally extends discontinuously along said equator line, such that a portion of said collum femur or prosthetic collum femur can be placed between said extension line and said equator line.

The extension line can be placed distal to the equator line, when the medical device is implanted.

The extending portion adapted to clasp the caput femur could comprise an elastic portion, which for example could comprise an elastic material, a spring or an elastic band.

The elastic band cold be adapted to at least partly encircle the caput femur.

According to another embodiment, the extending portion could comprise a movable portion adapted to clasp the caput femur, and further adapted to move such that said movable portion releases the caput femur or prosthetic caput femur from said medical device, when a predetermined strain is placed on said medical device.

According to yet another embodiment, the movable portion could comprise a movable part.

According to yet another embodiment, the extending portion could comprise at least one magnet adapted to hold the caput femur in the medical device.

According to yet another embodiment the extending portion could comprise a rupture device adapted to fail at a pre-determined strain. The rupture device could for example comprise a rupture band, or a rupture pin.

According to yet another embodiment, the extending portion could be adapted to slide against the caput femur, or adapted to roll against the caput femur. The extending portion adapted to roll against the caput femur could comprise a ball shaped part.

According to one embodiment, the at least one extending portion extends longitudinally along said equator line, dorsal to a lateral-medial axis of pelvis.

According to one embodiment, the at least one extending portion extends longitudinally along said equator line, dorsal to the lateral-medial axis and proximal to the lateral-medial axis of pelvis.

According to one embodiment, the at least one extending portion extends longitudinally along said equator line, dorsal to the lateral-medial axis and distal to the lateral-medial axis of pelvis.

According to one embodiment, the at least one extending portion extends longitudinally along said equator line, dorsal to the lateral-medial axis and distal to the lateral-medial axis of the pelvis, and one extending portion extends dorsal to the lateral-medial axis and proximal to the lateral-medial axis of the pelvis.

According to one embodiment, the at least one extending portion extends longitudinally along said equator line, in the proximal quadrant thereof.

According to one embodiment, the at least one extending portion extends longitudinally along said equator line, in the distal quadrant thereof.

According to one embodiment, the two extending portions extends longitudinally along said equator line, in the distal and proximal quadrant thereof.

The at least one extending portion could extend longitudinally along the equator line, in the proximal and dorsal quadrant thereof.

The at least one extending portion could extend longitudinally along said equator line, in the distal and dorsal quadrant thereof.

The at least one extending portion could extend longitudinally along the equator line, in the distal, dorsal and proximal quadrant thereof.

According to one embodiment, at least a first portion of the medical device is an extending portion, extending beyond the circular equator line, and at least a second portion is a portion not extending beyond the circular equator line, wherein said second portion longitudinally extends along at least ¼ of said circular equator line.

In any of the embodiments herein, the at least first portion of the medical device could be an extending portion, extending beyond said circular equator line, and at least a second portion could be a portion not extending beyond said circular equator line, wherein said second portion longitudinally extends along at least ⅓ of said circular equator line.

In any of the embodiments herein, the at least first portion of the medical device could be an extending portion, extending beyond said circular equator line, and at least a second portion could be a portion not extending beyond said circular equator line, wherein said second portion longitudinally extends along at least ½ of said circular equator line.

In any of the embodiments herein, the at least first portion of the medical device could be an extending portion, extending beyond said circular equator line, and at least a second portion could be a portion not extending beyond said circular equator line, wherein said second portion longitudinally extends along at least ¼ of said circular equator line.

In any of the embodiments herein, the at least first portion of the medical device could be an extending portion, extending beyond said circular equator line, and at least a second portion could be a portion not extending beyond said circular equator line, wherein said first portion longitudinally extends along at least ⅓ of said circular equator line.

In any of the embodiments herein, the at least first portion of the medical device could be an extending portion, extending beyond said circular equator line, and at least a second portion could be a portion not extending beyond said circular equator line, wherein said first portion longitudinally extends along at least ½ of said circular equator line.

In any of the embodiments herein, the at least first portion of the medical device could be an extending portion, extending beyond said circular equator line, and at least a second portion could be a portion not extending beyond said circular equator line, wherein said first portion longitudinally extends along at least 1/10 of said circular equator line.

In any of the embodiments herein, the at least one first portion of said medical device could be an extending portion, extending beyond said circular equator line, and at least a second portion could be a portion not extending beyond said circular equator line. The first portion could longitudinally extend along at least 1/10 of said circular equator line, and said second portion could longitudinally extend along at least ¼ of said circular equator line.

In any of the embodiments herein, the at least two first portions of said medical device could be extending portions, extending beyond said circular equator line, and at least a second portion could be a portion not extending beyond said circular equator line. The first portions each longitudinally extending along at least 1/10 of said circular equator line, and said second portion longitudinally extends along at least ¼ of said circular equator line.

According to one embodiment, the at least two first portions of the medical device could be extending portions, extending beyond the circular equator line, and wherein one of the extending portions extends further than the other extending portion.

The medical device could according to one embodiment further comprise two second portions not extending beyond said circular equator line. The two first extending portions could longitudinally extend along the equator line between the two second portions.

According to one embodiment, the medical device further comprises at least one hole adapted to receive a fixating member, for fixating said medical device to the pelvic bone. The hole could be adapted to receive a screw for fixating said medical device to the pelvis.

In yet another embodiment, the medical device could comprise at least one extending portion adapted to clasp the caput femur, or a prosthetic caput femur, for restraining said caput femur, or prosthetic caput femur in said medical device. The medical device could be adapted to release the caput femur or prosthetic caput femur from the medical device when a predetermined strain is placed on said medical device.

The extending portion could comprise an elastic portion, which for example could comprise an elastic material, a spring or an elastic band which could be adapted to at least partly encircle said ball shaped piece.

According to another embodiment, the extending portion could comprise a movable portion which could comprise a movable part.

According to another embodiment, the extending portion could comprise a magnet adapted to hold said first piece to said second piece.

According to yet another embodiment, the extending portion could comprise a rupture device adapted to fail at a pre-determined strain. The rupture device could for example comprise a rupture band or a rupture pin.

According to one embodiment, the medical device could comprises multiple holding members. Said multiple holding members could comprise at least one holding member adapted to slide against the caput femur, or prosthetic caput femur or at least one holding member adapted to roll against the caput femur, or prosthetic caput femur. The holding member adapted to roll could comprise a ball shaped holding member.

The medical device could according to any one of the preceding embodiments have at least one of extending portion, when implanted, is adapted to be placed such as to restrict the motion range of the hip joint, and wherein said at least one extending portion is adapted to be placed or shaped such that at least one of adduction, abduction, flexion, extension, a combination of flexion and adduction or abduction, a combination of extension and adduction or abduction, rotation in, rotation out, and any combination of rotation in or out and the other described movements, is restricted more degrees from maximal movement than any of the other.

According to one embodiment, the medical device comprises a prosthetic caput femur being ball shaped and adapted to be at least partly placed inside said inner surface, being bowl shaped, wherein: said inner surface comprises an equator line, being the largest circular circumference of said inner surface, said at least one extending portion of said inner surface passes beyond said equator line, such that the end portion of a contacting portion of said inner surface, the most distal portion of said inner surface adapted to contact the prosthetic caput femur, when the inner surface is placed symmetrically onto the prosthetic caput femur, forms a circular extension line parallel to said equator line having a smaller circumference than said equator line, and said at least one extending portion is constructed according to at least one of the following alternatives; a) circumferentially extends discontinuously along said equator line having enough circumferential distance lacking any extending portion and b) extends with different distal extension in different extending portions or part of such portion of said circumferential extension.

According to one embodiment medical device comprises an inner surface comprising an equator line, being the largest circular circumference of said inner surface. The at least one extending portion of said inner surface passes beyond said equator line, such that the end portion of a contacting portion of said inner surface, the most distal portion of said inner surface adapted to contact a prosthetic caput femur, when the inner surface is placed symmetrically onto the prosthetic caput femur, forms a circular extension line parallel to said equator line having a smaller circumference than said equator line, and said at least one extending portion extends with different distal extension over the circumferential extension, thus adapted to restrict movements clearly different in different directions of movement, due to different distal extension of different extending portions in said circumferential extension.

According to another embodiment, the medical device comprises an inner surface comprising an equator line, being the largest circular circumference of said inner surface, at least one extending portion of said inner surface passes beyond said equator line, such that the end portion of a contacting portion of said inner surface, the most distal portion of said inner surface adapted to contact a prosthetic caput femur, when the inner surface is placed symmetrically onto the prosthetic caput femur, forms a circular extension line parallel to said equator line having a smaller circumference than said equator line, and part of said at least one extending portion extends with different distal extension over the circumferential extension, thus adapted to restrict movements clearly different in different directions of movement, due to different distal extension of different parts of such extending portion in said circumferential extension.

According to one embodiment the medical device for implantation in a hip joint comprises a locking member for locking an artificial replacement of an acetabulum in a hip joint to clasp a caput femur or an artificial replacement therefore, when implanted in a hip joint of a patient, wherein said locking member is adapted to in situ assist in the fixation of the medical device, wherein: said inner surface comprises an equator line, being the largest circular circumference of said inner surface, at least one extending portion of said inner surface passes beyond said equator line, such that the end portion of a contacting portion of said inner surface, the most distal portion of said inner surface adapted to contact a caput femur or prosthetic caput femur, when the inner surface is placed symmetrically onto the prosthetic caput femur, forms a circular extension line parallel to said equator line having a smaller circumference than said equator line, said locking member is adapted to lock said caput femur or prosthetic caput femur such that the caput femur or prosthetic caput femur remains clasped and restrained in said inner surface, and said locking member is adapted to lock said at least one extension portion, when implanted, having at least the end portion of the extension portion radially fixed within said circular extension line.

According to one embodiment the locking member is adapted to lock in at least a first and second locking position.

According to one embodiment the locking member is adapted to lock in at least a first and a second locking position, and wherein said locking member is adapted to; in said first locking position, lock an artificial caput femur surface having at least one extending portion, to a first size caput and/or collum femur, and in said second locking position, lock said artificial caput femur surface, to a second smaller size caput femur and/or collum femur.

The hip joint having a collum femur, having a first axial distribution leading to a caput femur, wherein said collum femur is placed distal to the caput femur, a center axis of the collum and caput femur in line with the first axial distribution being the caput femur center axis, wherein the caput femur has a substantially ball shaped configuration with an outer maximum radius perpendicular to the caput femur center axis, the caput femur being placed in a bowl shaped acetabulum, having an opening, wherein the bowl shaped acetabulum has a second axial distribution with an acetabulum center axis from the center of the bottom of the acetabulum bowl and following the center of the bowl towards the center of the opening of the bowl, towards the caput femur, wherein the acetabulum bowl has an inner maximum radius perpendicular to the acetabulum center axis, wherein the caput femur center axis is in line/aligned with the acetabulum center axis, in a special centered position, when the caput femur is placed; aligned, centered and symmetrical in the acetabulum bowl in the hip joint, the aligned center axis is defined as the hip joint center axis, wherein the caput femur and the acetabulum has one hip joint surface each, placed towards and contacting each other, wherein the hip joint surfaces carrying weight in the hip joint are the weight carrying surfaces, wherein the outer maximum radius of the caput femur is forming a circular extending, maximum caput femur radius circle, extending perpendicular to the hip joint center axis, defining a maximum caput femur radius cross-section perpendicular to the hip joint center axis, wherein: said medical device comprises at least one artificial hip joint surface, adapted to at least partly replace at least one of the hip joint surfaces, said artificial hip joint surface at least partly being hollow and having an inner and outer surface, wherein said artificial hip joint surface has an artificial hip joint surface center axis aligned with the hip joint center axis when the hip joint is placed in the special centered position, when at least one of said artificial hip joint surfaces is implanted in the hip joint, with the caput femur or an artificial caput femur surface placed; aligned, centered and symmetrical in the acetabulum bowl or an artificial acetabulum surface in the hip joint, wherein said medical device comprises a central part and a surrounding part, the central part being aligned with the artificial hip joint surface center axis and the surrounding part surrounding the surface of the caput femur or an artificial caput femur surface not including the central part, wherein the caput femur or an artificial caput femur surface, has a maximum caput femur radius cross-section, in which the outer maximum radius of the caput femur or said artificial caput femur surface is forming a circular extending maximum caput femur or artificial caput femur radius circle, extending perpendicular to the hip joint center axis, defining the maximum caput femur radius cross-section perpendicular to the hip joint center axis or perpendicular to said artificial hip joint surface center axis, when the hip joint is placed in said special centered position, wherein the surrounding part of said at least one artificial hip joint surface comprises at least one first extending portion of the artificial hip joint surface for extending in distal direction at least partly beyond the maximum caput femur radius cross-section, when the hip joint is placed in said special centered position, when at least one of the artificial hip joint surfaces is implanted in the hip joint, wherein said at least one first beyond part is adapted to have a closest perpendicular distance to said artificial hip joint surface center axis, being smaller than an inner maximum distance, extending perpendicularly from said artificial hip joint surface center axis to said inner surface of said artificial hip joint surface, when the hip joint is placed in the above mentioned special centered position and said artificial hip joint surface is placed in a functional position in the hip joint, thus adapted to create and creating a more stable position of said artificial hip joint surface when mounted in the hip joint.

According to one embodiment, the hip joint has a caput femur hip joint surface partly being the contacting surface of the hip joint, the hip joint further having a collum femur, having a first axial distribution leading to a caput femur, wherein a center axis of the first axial distribution of the collum femur and the caput femur, being the caput femur center axis, wherein the collum femur is placed more distal than caput femur, wherein; said medical device comprises an artificial caput femur surface being hollow, having a major opening adapted to be directed towards the caput femur or a surgically modified caput femur, wherein said artificial caput femur surface is adapted to replace a caput femur hip joint surface, wherein said artificial caput femur surface further having; a medical device caput center axis passing through said major opening being aligned with the caput femur center axis, when said medical device is implanted in a functional position in the hip joint, wherein said medical device comprises a central part and a surrounding part, the central part being aligned with the medical device center axis and the surrounding part surrounding the surface of the caput femur or the surgically modified caput femur not including the central part, and wherein said medical device further comprising an inner surface adapted to have a first distal distance extending perpendicularly from said medical device caput center axis to said inner surface of the surrounding part of said artificial caput femur surface, said first distal distance being shorter than a second proximal distance extending perpendicularly from said medical device caput center axis to said inner surface of said artificial caput femur surface, said second proximal distance extending from a more proximal position on said medical device caput center axis than said first distal distance, being the second proximal distance, when said artificial caput femur surface is implanted in said functional position in the hip joint.

The hip joint has an acetabulum, being a bowl shaped contacting surface of the hip joint comprising a substantially circular major opening in distal direction of the acetabulum in the hip joint and a bottom center point in said bowl shaped acetabulum proximally in the hip joint, wherein an acetabulum center axis extends from the bottom point through the center point of the substantially circular opening, wherein the acetabulum has a weight carrying surface contacting a ball shaped caput femur located in the acetabulum bowl in the hip joint, wherein the caput femur is connected to the collum femur, and the collum femur has a center axis aligned with a caput femur center axis, wherein; said medical device comprises an artificial acetabulum surface adapted to replace the weight carrying surface of the acetabulum, wherein said artificial acetabulum surface is hollow and has a major acetabulum opening adapted to be directed towards the caput femur or an artificial replacement of at least the surface of the caput femur, wherein said artificial acetabulum surface is adapted to receive a caput femur or an artificial replacement of at least the surface of the caput femur, in said hollow artificial acetabulum surface, when implanted in the hip joint, said artificial acetabulum surface having; a medical device acetabulum center axis, adapted to be aligned with the acetabulum center axis, when said artificial acetabulum surface is placed in the hip joint, and an inner surface adapted to have a first distal distance extending perpendicularly from said medical device acetabulum center axis, to said inner surface of said artificial acetabulum surface, said first distal distance being shorter than a second proximal distance extending perpendicularly from said medical device acetabulum center axis to said inner surface of said artificial acetabulum surface, said second proximal distance extending from a more proximal position on said medical device acetabulum center axis than said first distal distance, when said artificial acetabulum surface is implanted functionally in the hip joint, wherein said artificial acetabulum surface is adapted to receive in the hollow artificial acetabulum surface the caput femur or an artificial replacement of at least the surface of the caput femur, when implanted in the hip joint, for achieving a functional hip joint.

According to one embodiment the least one of extending portion is adapted to have at least one of its shape or position such that the restriction of movement range of the hip joint, in degrees from maximal movement, is restricted more in at least one predefined direction than in any other direction, when implanted.

A method using a medical device according to any of the preceding claims is further provided. The method comprise cutting the skin in the hip region dissecting the hip joint implanting the medical device in a hip joint of a patient, fixating the device to the pelvic bone of the patient, and wherein said medical device comprises an inner and an outer surface, having a contacting portion of said inner surface being spherical and bowl shaped facing the inner surface to the center of the hip joint having at least one extending portion, extending a contacting portion for contacting the caput femur or a prosthetic replacement therefore, placing a caput femur or a prosthetic replacement therefore having a spherical portion, such that said extending contacting portion of said inner surface is clasping said spherical portion of said caput femur, or a prosthetic replacement therefore, such that said caput femur, or a prosthetic replacement therefore is restrained in said bowl shaped inner surface.

According to one embodiment the method comprises. placing for contacting towards said inner surface said caput femur or artificial replacement therefore, said inner surface comprising an equator line being the largest circular circumference of said inner contacting surface, placing and passing with said at least one extending portion beyond said equator line, such that the end portion of said contacting portion of said inner surface forms a circular extension line having a parallel smaller circumference than said equator line, the end portion being the most distal portion of the inner surface being in contact with said caput femur or artificial replacement therefore, when said caput femur or artificial replacement therefore is placed symmetrically in said inner surface, and wherein said at least one extending portion is extending circumferentially discontinuously along said equator line, such that the method involves, placing a portion of said collum femur or prosthetic replacement therefore between said extension line and said equator line when moving said caput femur or artificial replacement therefore in relation to said inner surface.

According to one embodiment, the said at least one extending portion is mounted according to at least one of the following alternatives: a) extending circumferentially discontinuously along said equator line having enough circumferential distance lacking any extending portion and b) extending with different distal extension in different extending portions or part of such portion of said circumferential extension.

According to one embodiment the method comprises using a medical device for implantation in a hip joint according to any of the preceding claims, comprising a locking member for locking an artificial replacement of an acetabulum in a hip joint to clasp a caput femur or an artificial replacement therefore, when implanted in a hip joint of a patient, wherein said locking member is adapted to in situ assist in the fixation of the medical device, said artificial acetabulum comprising an inner surface comprising an equator line, being the largest circular circumference of said inner surface, wherein at least one extending portion of said inner surface passes beyond said equator line, such that the end portion of a contacting portion of said inner surface, the most distal portion of said inner surface adapted to contact a caput femur or artificial caput femur forms a circular extension line parallel to said equator line having a smaller circumference than said equator line, when the inner surface is placed symmetrically onto the prosthetic caput femur, wherein the method comprising the following steps: cutting the skin in the hip region dissecting the hip joint implanting the medical device in a hip joint of a patient, fixating the artificial replacement of an acetabulum to the pelvic bone of the patient, comprising an inner and an outer surface, having a contacting portion of said inner surface being spherical and bowl shaped, facing the inner surface to the center of the hip joint having at least one extending portion, extending a contacting portion for contacting the caput femur or a prosthetic replacement therefore, placing a caput femur or an artificial replacement therefore having a spherical portion, such that said extending contacting portion of said inner surface is clasping said spherical portion of said caput femur, or an artificial replacement therefore, placing said locking member such that said caput femur, or artificial replacement therefore is restrained in said bowl shaped inner surface, and locking said caput femur or artificial caput femur in said clasped and restrained position in said inner surface, by fixating radially at least the end portion of the at least one extension portion within said circular extension line.

According to one embodiment the method comprises clasping said caput femur or artificial replacement therefore in said medical device inner surface, and releasing said caput femur or artificial replacement therefore when a predetermined strain is placed onto said clasped caput femur or artificial replacement therefore.

Please note that any embodiment or part of embodiment, feature, method, associated system, part of system described herein or in the associated figures may be combined in any way.

BRIEF DESCRIPTION OF DRAWINGS

The invention is now described, by way of example, with reference to the accompanying drawings, in which:
FIG. 5 shows the medical device according to one embodiment, when fixated to the pelvic bone,
FIG. 16 shows the hip joint in section when a medical device is implanted, in its first state,
FIG. 17 shows the hip joint in section when a medical device is implanted, in its second state,
FIG. 18 shows the medical device in section, when in its first state.

DETAILED DESCRIPTION

Figure 1:
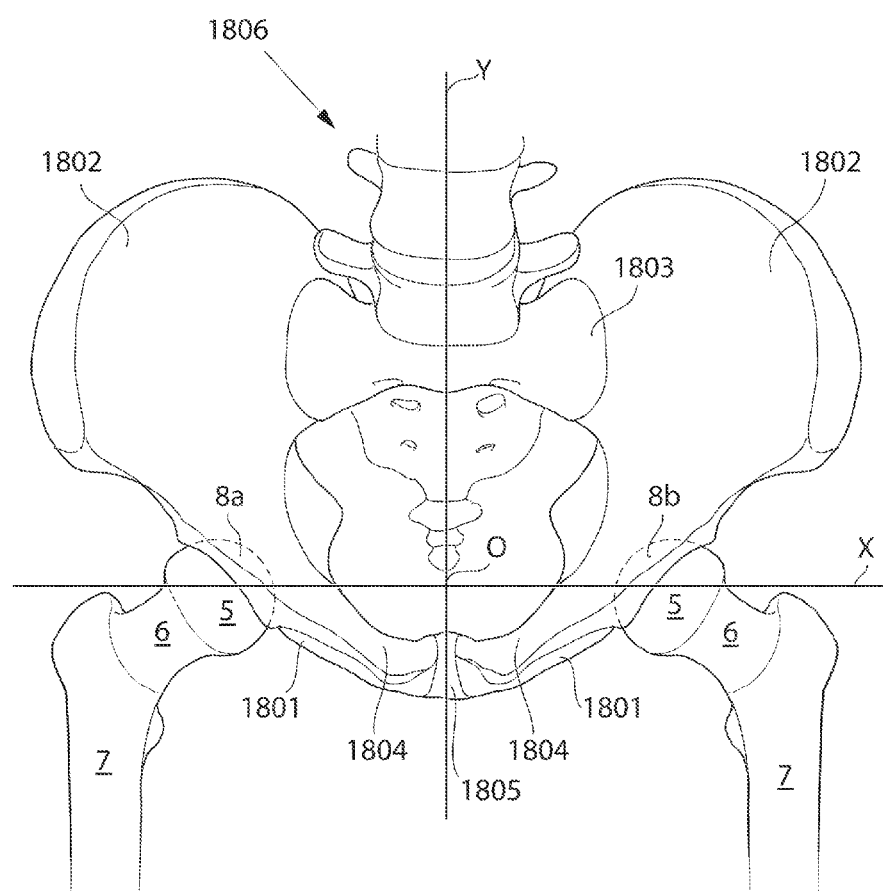
FIG. 1 shows pelvis in a frontal view.

The hip joint is a synovial ball and socket joint which permits a large motion range for allowing a plurality of different movements of the lower limb. From a neutral position the following movements of the hip joint are normally possible: Lateral or external rotation, 30° with the hip extended, 50° with the hip flexed, medial or internal rotation 40°, extension or retroversion 20°, flexion or anteversion 140°, abduction 50° with hip extended, 80° with hip flexed, adduction 30° with hip extended, 20° with hip flexed.

When replacing the natural hip joint with a prosthetic hip joint, the depth of the prosthetic acetabulum will affect the motion range, the deeper the acetabulum bowl is made the more restrictive it is to the motion range. A deeper bowl has the advantage of reducing the risk of hip joint luxation, the risk of which is a major drawback with prosthetic hips of today.

The anatomy of the hip joint and its surroundings is further disclosed in: Marieb et al., Human Anatomy, 2003, Benjamin Cummings, San Francisco, pages 195-202 and in Moore et al., Clinically oriented anatomy, 1999, Lippincott, Williams & Wilkins, Baltimore, pages 501-653, both hereby incorporated by reference.

Functional hip movements are to be understood as movements of the hip that at least partly correspond to the natural movements of the hip. On some occasions the natural movements of the hip joint might be somewhat limited or altered after hip joint surgery, which makes the functional hip movements of a hip joint with prosthetic surfaces somewhat different than the functional hip movements of a natural hip joint.

Everyday activities is to be understood as activities which are not connected to any extreme movements, such that some physical sports require. For example, everyday activities comprise: walking, sitting, cycling etc.

The functional position of an implantable medical device or prosthesis is the position in which the hip joint can perform functional hip movements. The final position is to be understood as a functional position in which the medical device needs no further position change to function.

Elastic deformation is when a material deforms under stress (e.g. external forces), but returns to its original shape when the stress is removed. A more elastic material is to be understood as a material having a lower modulus of elasticity. The elastic modulus of an object is defined as the slope of its stress-strain curve in the elastic deformation region. The elastic modulus is calculated as stress/strain, where stress is the force causing the deformation, divided by the area to which the force is applied; and strain is the ratio of the change caused by the stress.

Elasticity is to be understood as a materials ability to deform in an elastic way.

Stiffness is to be understood as the resistance of an elastic body to deformation by an applied force.

Biocompatible material is to be understood as being a material with low level of immune response. Biocompatible materials are sometimes also referred to as biomaterials. Analogous is biocompatible metals a biocompatible metal with low immune response such as titanium or tantalum. The biocompatible metal could also be a biocompatible alloy comprising at least one biocompatible metal.

Form fitting is to be understood as an element having a part or section which is adapted to enable a mechanical connection of said element to at least one other element using said part or section. Form fitted structure is a structure of an element which enables form fitting.

In the following a detailed description of embodiments of the present invention will be given. In the drawing figures, like reference numerals designate identical or corresponding elements throughout the several figures. It will be appreciated that these figures are for illustration only and are not in any way restricting the scope of the invention. Thus, any references to direction, such as "up" or "down", are only referring to the directions shown in the figures. Also, any dimensions etc. shown in the figures are for illustration purposes.

FIG. 1 shows the pelvis in a frontal view. Pelvis comprises the right and left hip bone making up the pelvic bone, in turn comprising the Sacrum 1803, Ilium 1802, Pubis 1804 and Ischium 1801. The hip joint houses the right and left acetabulum 8a,b placed laterally and distally in the pelvis. The acetabulum 8a,b being a spherically shaped cavity in the hip bones making up one of the parts of the hip joint, the acetabulum 8a,b being adapted to house the caput femur 5, being the proximal portion of the femoral bone 7 having a spherical contacting surface adapted to be placed in the acetabulum 8a,b and thus creating the operable hip joint. The pelvis has a lateral-medial axis X extending substantially from the bottom of the left acetabulum 8a to the bottom of the right acetabulum 8b, the pelvis further having a proximal-distal Y axis extending perpendicular to said lateral-medial axis, centrally and substantially along the length of the patient, passing the dorsal portions of the pubic symphysis 1805 and substantially following the spinal cord 1806, intersecting the lateral-medial axis X.

Figure 2A:
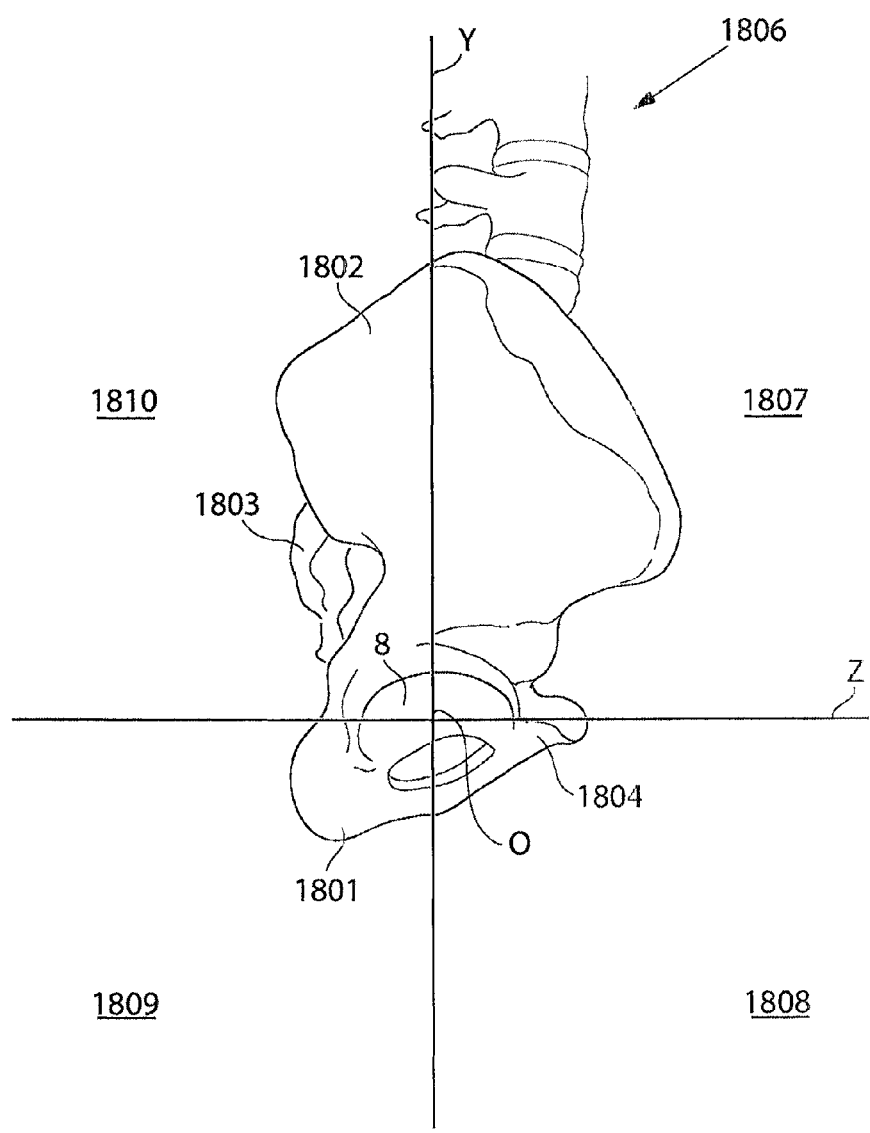
FIG. 2a shows pelvis in a lateral view.

FIG. 2a shows the pelvis in a lateral view, thus displaying the posterior side of Ilimu 1802, the anterior side of Ichum 1801, the anterior side of Pubis 1804, and Sacrum 1803 in a strict lateral view. The pelvis has furthermore a frontal-dorsal axis Z being perpendicular to the proximal-distal axis Y and the lateral-medial axis shown in FIG. 1, and intersecting them both creating a common origin O for the three axis X,Y,Z. The frontal-dorsal axis Z and the proximal-distal axis Y thus being oriented such that a first plane PZ, extending from the frontal-dorsal axis Z, and a second plane PY, extending from the proximal-distal axis Y, penetrates through the acetabulum 8, thus dividing the acetabulum 8 into 4 sections 1807, 1808, 1809 and 1810.

Figure 2B:
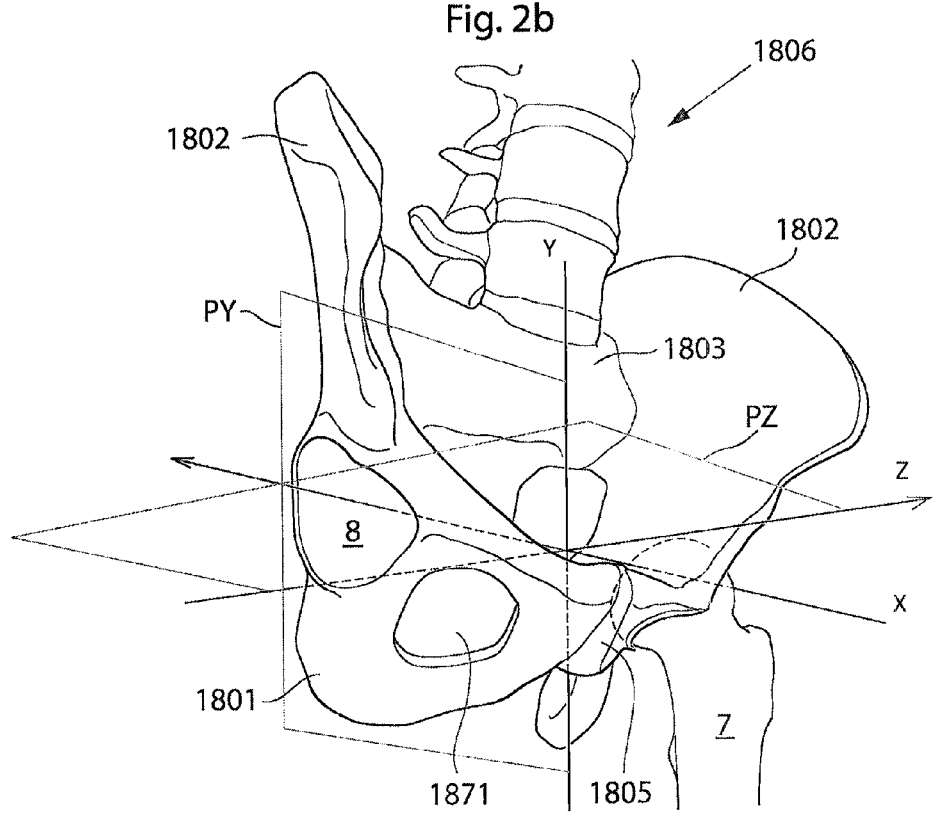
FIG. 2b shows pelvis in a perspective view from below.

FIG. 2b shows the pelvis in a perspective view from below displaying the lateral-medial axis X passing through the center of the right and left acetabulum 8. The lateral-medial axis X is perpendicular to the frontal-dorsal axis Z which also is perpendicular to the proximal-distal axis Y. A first plane PY extends from the proximal-distal axis Y, thus dividing the acetabulum in half, centrally. A second plane PZ extends from the dorsal-frontal axis Z, thus dividing the acetabulum in half, centrally and perpendicularly to the first plane PY.

Figure 2C:
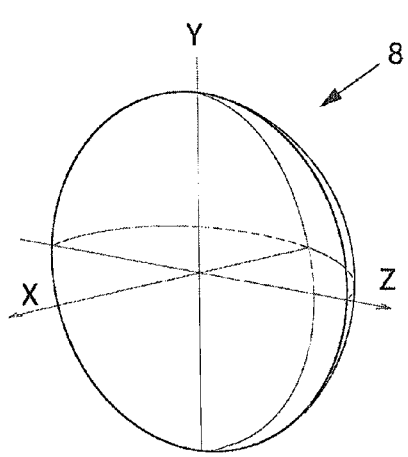
FIG. 2c shows the acetabulum, schematically.
Figure 2D:
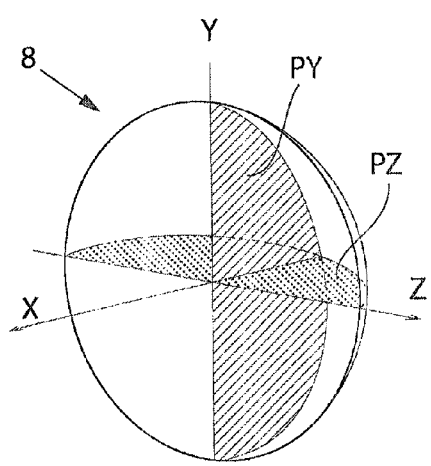
FIG. 2d shows the acetabulum, schematically.

FIGS. 2b and 2c shows the acetabulum 8 schematically, and how the planes PY, PZ divides the acetabulum in to quarters with axis X,Y,Z parallel to the X,Y,Z axis disclosed previously. FIG. 2b further discloses foramen obturatum 1871.

Figure 3:
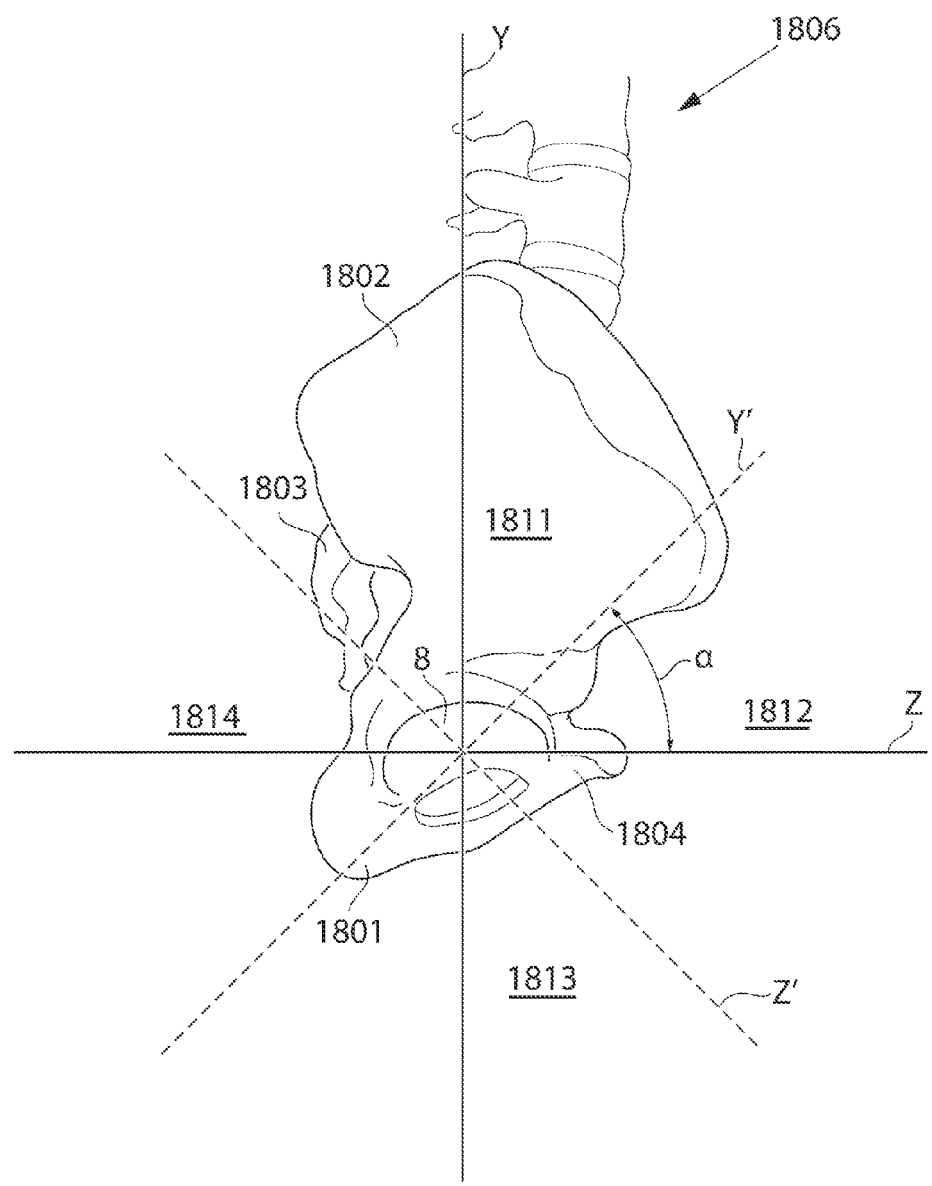
FIG. 3 shows the pelvis in a lateral view.

FIG. 3 shows a lateral view of the pelvis and further displaying two perpendicular axis Y' and Z' being two axis with the same origin as the axis Y and Z, but rotated clockwise at an angle α being 45°. The two axis Y' and Z' thus dividing the acetabulum 8 into quadrants 1811, 1812, 1813 and 1814. The quadrants being a proximal quadrant 1811, a frontal quadrant 1812, a distal quadrant 1813 and a dorsal quadrant 1814.

Figure 4:
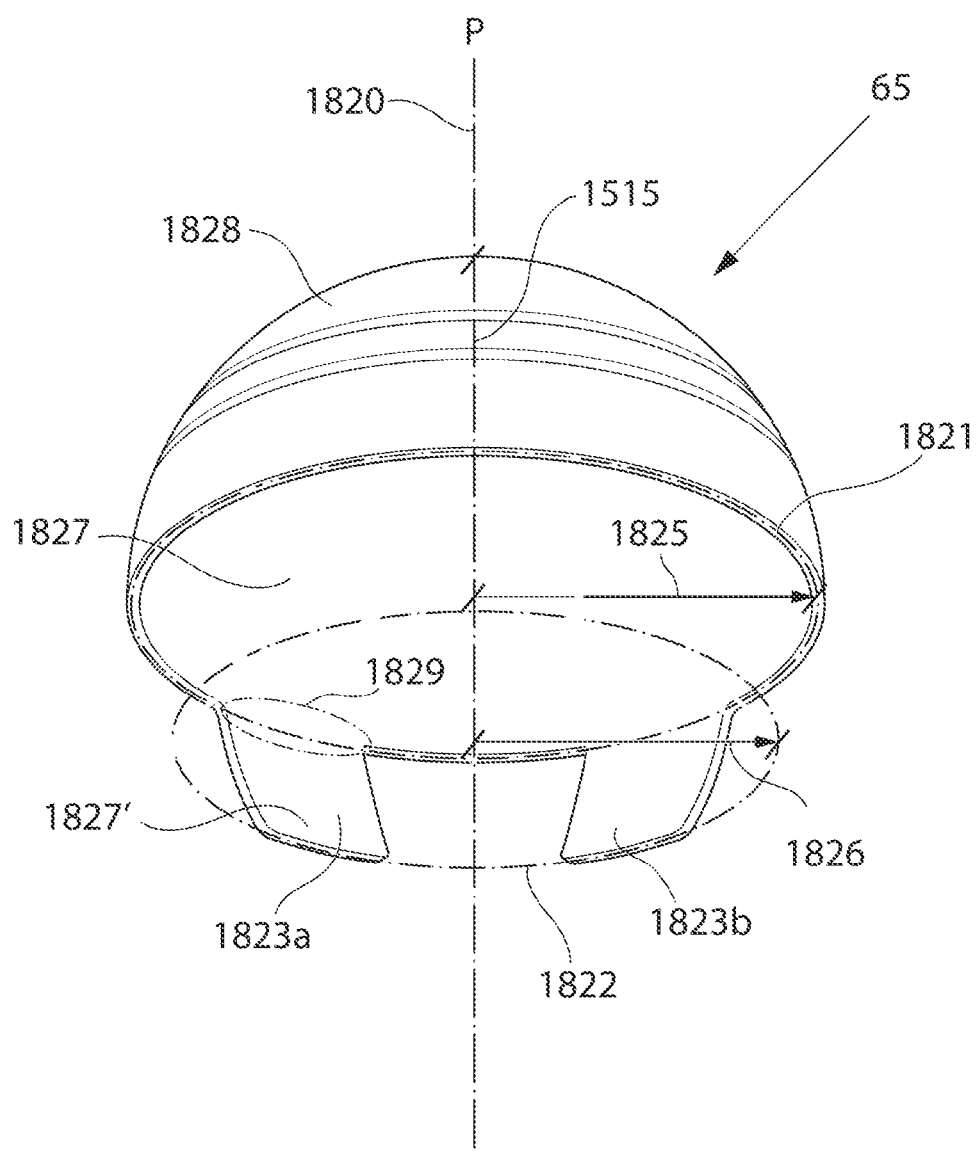
FIG. 4 shows the medical device according to one embodiment, in a perspective view.

FIG. 4 shows a medical device for implantation in a hip joint of a patient. The medical device is adapted to be fixated to the pelvic bone of the patient for example by means of an adhesive, such as bone cement, or mechanical fixating members, such as orthopedic screws. The medical device comprises an inner 1827 and an outer 1828 surface. A contacting portion of the inner surface 1827 is spherical and faces the center of the hip joint, when the medical device is implanted. The inside of the medical device is adapted to receive a caput femur or a prosthetic replacement therefor having a spherical portion, and the spherical contacting portion of the inner surface 1827 is adapted to be in contact with a spherical portion of the outer surface of the caput femur or a prosthetic replacement therefor. The medical device, according to the embodiment shown in FIG. 4 comprises two extending portions 1823a,b, extending the contacting portion of the inner surface 1827' such that the extending portions 1823a,b clasps the spherical portion of caput femur or a prosthetic replacement therefor, for restraining the spherical portion in the medical device. The medical device is adapted to receive the caput femur or a prosthetic replacement therefor, having a collum femur or prosthetic collum femur fixated to the spherical portion of the caput femur or prosthetic replacement therefor. The inner surface 1827 comprises an equator line 1821, being the largest circular circumference of the inner surface. The two extending portions passes beyond the equator line 1821, such that and end portion 1829 of the contacting portion, here being of the extending portion 1823b of the inner surface 1827, forms a circular extension line 1822 placed distal to the equator line 1821, when the medical device is implanted, and having a smaller circumference than the equator line 1821; thus a distance 1826 between a center axis P of the medical device and the extension line 1822 is shorter than a distance 1825 between the center axis P and the equator line 1821.

FIG. 5 shows the medical device described with reference to FIG. 4 when implanted. According to this embodiment the medical device is adapted to be fixated using orthopedic screws 1830, mechanically fixating the medical device to the pelvic bone 9, by the medical device comprising holes through which the screws 1830 are placed. In FIG. 5 the contacting portion of the inner surface 1827 has been placed in contact with the spherical portion of a prosthetic caput femur 5 being fixated to a prosthetic collum femur 6, the prosthetic caput 5 and collum 6 femur replacing the proximal portion of the femoral bone. The two extending portions 1823a and 1823b extending the contacting portion of the inner surface and clasps the spherical portion of the prosthetic caput femur 5, for restraining the spherical portion in the medical device. The inner surface comprising the equator line 1821, and the extending portions 1823a,b passing beyond the equator line 1821 and comprising the more distal extension line 1822 having a smaller circumference than the equator line 1821. The more distal extension line 1822 being placed at a distance D1 from the equator line 1821. According to this embodiment the extension line 1822 is parallel to the equator line 1821, however this is not necessarily so in other embodiments.

The extension portion 1823a according to the embodiment shown in FIG. 5 extends longitudinally along the equator line, a distance D2. Along another portion of the equator line, a distance D3, there are no extending portion, which enables the collum femur 6 to enter the space between the first and second extending portions 1823a,b which creates a larger movement range of the hip joint.

The extending portions thus extending discontinuously along the equator line 1821, such that a portion of the collum femur 6 can be placed between the extension line 1822 and the equator line 1821.

The extending portion, according to any of the embodiments, adapted to clasp the caput femur or prosthetic replacement therefor for restraining the caput femur or prosthetic replacement therefor in the medical device, could further be adapted to release the caput femur or prosthetic replacement therefor when a large enough strain is placed on the joint. This feature enables the caput femur or prosthetic replacement therefor to be fixedly attached in the medical device in normal use and be released from the medical device e.g. in case of an accident, thus reducing the risk of damaging the bodily structures, such as the femoral bone, or the fixations between bodily structures and prosthetic parts, such as the fixation between the femoral bone and a prosthetic stem to which the prosthetic collum and caput femur is fixated.

According to one embodiment the extending elements, as for example disclosed with reference to FIGS. 1-5, are placed such that the extending elements restricts the motion range minimally, or in ways which are not limiting the motion range used in everyday life. The hip joint is a synovial ball and socket joint which permits a large motion range for allowing a plurality of different movements of the lower limb. From a neutral position the following movements of the hip joint are normally possible: Lateral or external rotation, 30° with the hip extended, 50° with the hip flexed, medial or internal rotation 40°, extension or retroversion 20°, flexion or anteversion 140°, abduction 50° with hip extended, 80° with hip flexed, adduction 30° with hip extended, 20° with hip flexed. In the movement ranges of abduction and adduction the depth of the acetabulum bowl and thus the extending portions does not restrict the motion range in a critical way since the motion range of the normal hip is restricted in these movements, in normally agile persons, by the muscles, tenors and ligaments surrounding the hip joint.

Figure 6A:
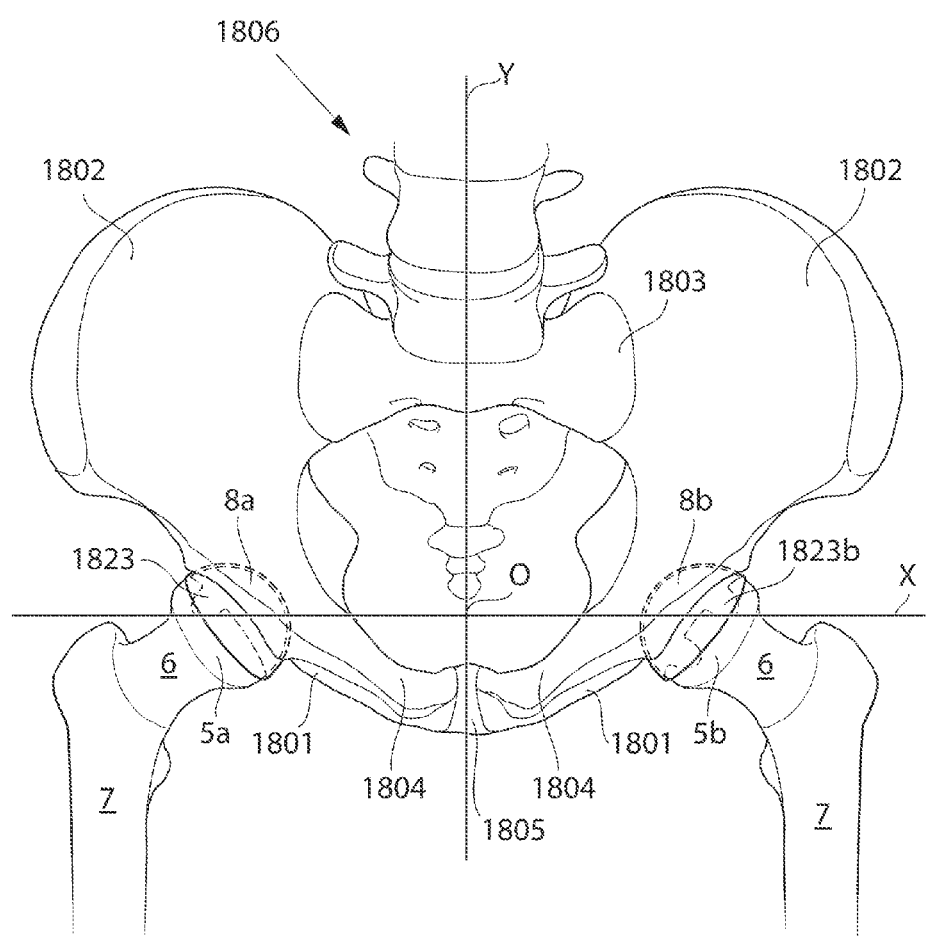
FIG. 6a shows pelvis in a frontal view, when medical device according to two embodiments have been implanted.

FIG. 6a shows a frontal view of pubis and the proximal portions of the femoral bones 7 when two embodiments of the medical device has been implanted in the hip joint. The medical device shown placed on the right caput femur 5a and placed in the right acetabulum 8a comprises one extending portion 1823, here placed dorsal to the proximal-distal axis Y, thus only partially limiting abduction in far excess of 50°. According to the embodiment shown, the extending portion 1823 extends longitudinally along the equator line 1821 about ⅒ of the length of the equator line 1821, however in other embodiments the extending portion 1823 extends along as much as half of the length of the equator line 1821, and in other embodiments the extending portion 1823 extends as little as about ⅓₀ of the length of the equator line 1821. The medical device shown placed on the left caput femur 5b and placed in the left acetabulum 8b comprises two extending portions 1823a,b, both being placed dorsal to the proximal-distal axis Y, when implanted, thus limiting the motion range of the hip joint in a non restrictive way, in relation to everyday activities. In both the right and left embodiment the extending portions 1823 extends discontinuously along the equator line 1821 thus enabling the collum femur 6 to partially be placed between the equator line and the extension line, and in the left embodiment, placed between the extending portions 1823a,b thus entering the cavity between the extending portions 1823a,b.

Figure 6B:
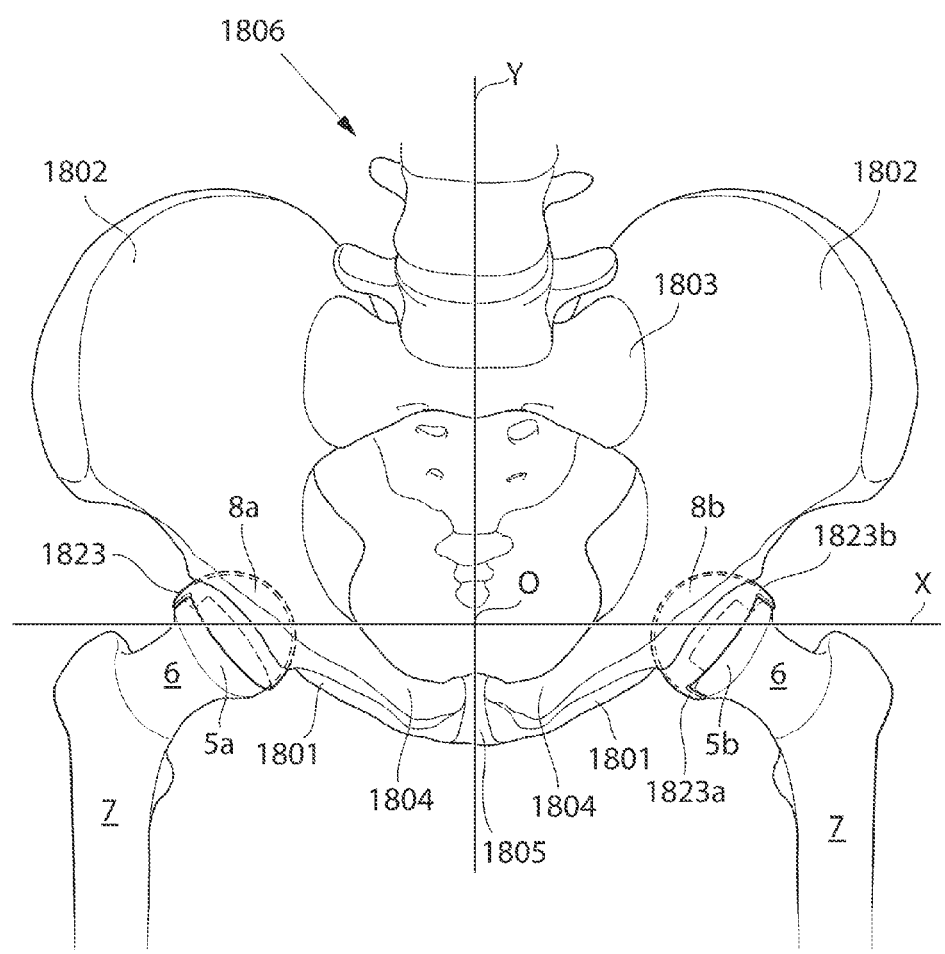
FIG. 6b shows pelvis in a frontal view, when medical device according to two further embodiments have been implanted.

FIG. 6b shows a frontal view of pubis and the proximal portions of the femoral bones 7 when two further embodiments of the medical device have been implanted in the hip joint. The medical device shown placed on the right caput femur 5a and placed in the right acetabulum 8a comprises one extending portion 1823, here placed in the proximal quadrant, which is further disclosed with reference to FIG. 3, thus limiting the motion range of the hip joint in a non restrictive way, in relation to everyday activities. According to the embodiment shown, the extending portion 1823 extends longitudinally along the equator line 1821 about ⅒ of the length of the equator line 1821, however in other embodiments the extending portion 1823 extends along as much as half of the length of the equator line 1821, and in other embodiments the extending portion 1823 extends as little as about ⅓₀ of the length of the equator line 1821. The medical device shown placed on the left caput femur 5b and placed in the left acetabulum 8b comprises two extending portions 1823a,b, being placed in the proximal and distal quadrants, thus limiting the motion range of the hip joint in a non restrictive way, in relation to everyday activities.

Figure 7:
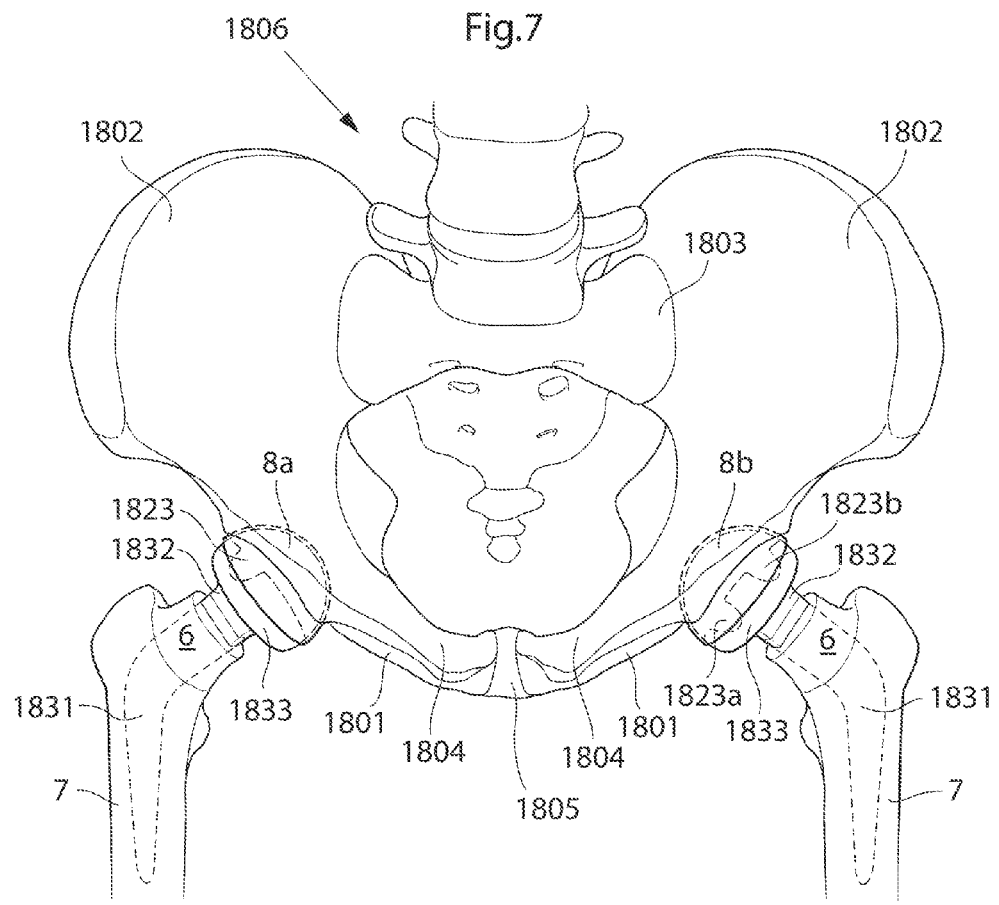
FIG. 7 shows pelvis in a frontal view, when medical device according to two embodiments have been implanted.

FIG. 7 shows the pelvis and the proximal portions of the femoral bones 7 including the embodiment of FIG. 6a, with the difference that the natural caput femur and a portion of the natural collum femur has been replaced by a prosthetic caput femur 1833 and a prosthetic collum femur 1832. The prosthesis further comprises a prosthetic stem 1831 adapted to be placed inside and fixated to the femoral bone, either using bone cement or by the surface of the stem being adapted to facilitate the growth-in of bone, thus fixating the stem. The prosthetic collum femur 1832 could be coordinated with the extending portions 1823 of the medical device for further improving the motion range of the hip joint, or not limiting the natural motion range of the hip joint.

Figure 8:
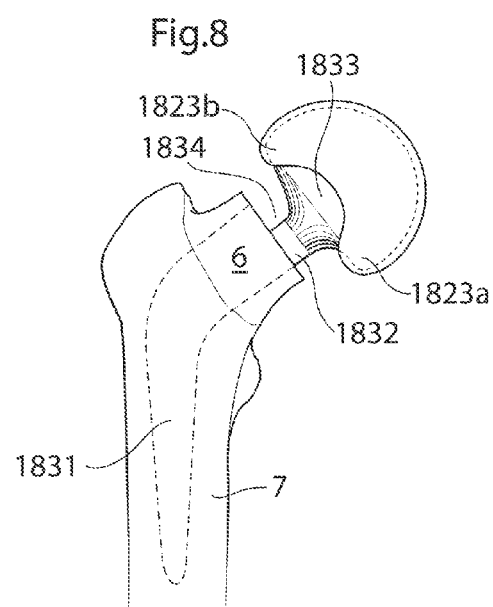
FIG. 8 shows a medical device according to one embodiment, when placed on a prosthetic caput femur fixated in the femoral bone.

FIG. 8 shows the medical device according to an embodiment in which the medical device comprises two extending portions 1823a,b. The medical device is placed on a prosthetic collum femur 1832, to which a prosthetic caput femur 1833 is attached. The prosthesis further comprises a stem 1831 which is adapted to be fixated inside of the femoral bone 7. The prosthetic collum femur 1832 is here adapted to further improve the motion range of the hip joint, or not limiting the natural motion range of the hip joint, by the prosthetic collum femur 1832 comprising a cavity 1834 in which the extending portions 1823 can be placed.

Figure 9A:
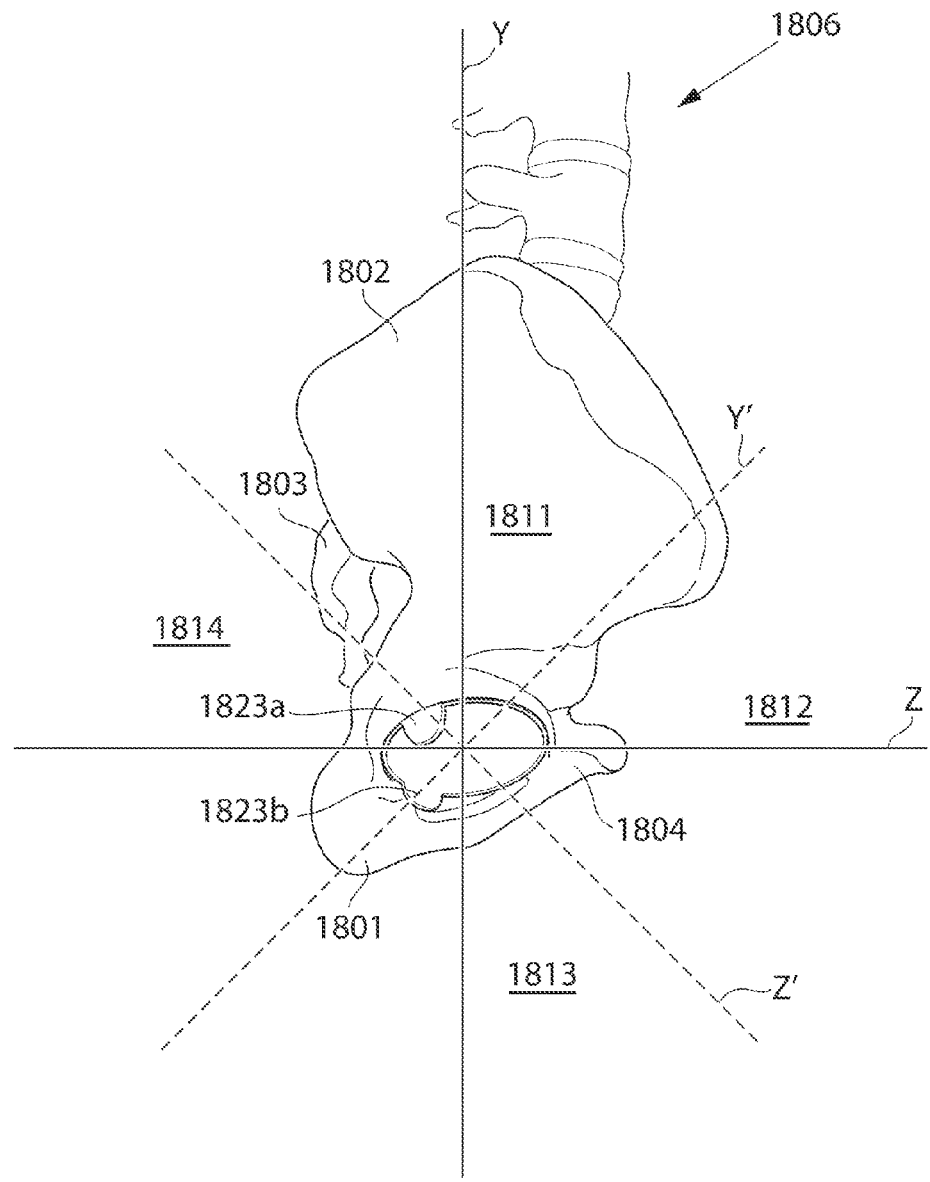
FIG. 9a shows pelvis in a lateral view, when the medical device is implanted.

FIG. 9a shows the pelvis in a lateral view, the medical device comprises two extending portions 1823a,b, both extending longitudinally along the equator line (as disclosed in for example FIG. 5) dorsal to the proximal-distal axis Y and being adapted to clasp the caput femur or a prosthetic replacement therefor. The extending portions 1823a,b extending dorsal to the proximal-distal axis Y and thus reducing the limiting effect that the extending portions 1823a,b, have on the motion range of the hip joint. According to the embodiment shown in FIG. 9a the extending portion 1823a placed proximally in the acetabulum extends longitudinally a distance of about ¼ of the length of the equator line, and the extending portion 1823b placed distally in the acetabulum extends longitudinally a distance of about ⅒ of the length of the equator line, however it is equally conceivable that this relationship is the other way around, or that any of the extending portions longitudinally extends a distance of as much as half of the length of the equator line, thus extending the entire distance of the equator line being dorsal to the proximal-distal axis, or that any of the extending portions 1823a,b extends a distance being as little as ⅓₀ of the distance of the equator line. According to the embodiment shown in FIG. 9a, the first extending portion 1823a extends in distal-lateral direction from the acetabulum, and the second extending portion 1823b extends medially towards foramen obturatum.

Figure 9B:
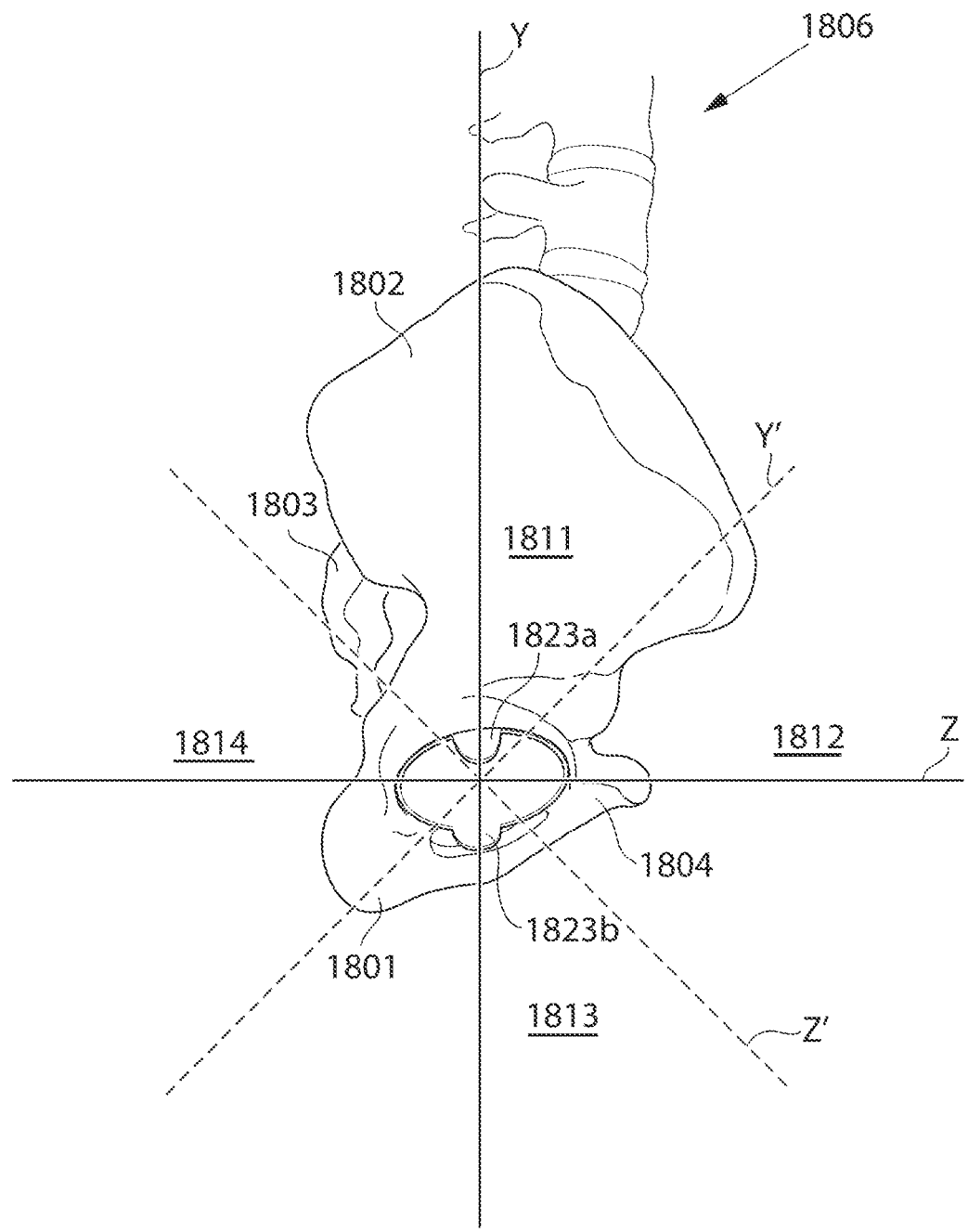
FIG. 9b shows pelvis in a lateral view, when the medical device is implanted.

FIG. 9b shows the pelvis in a lateral view, the medical device comprises two extending portions 1823a,b, the two extending portions 1823a,b extends in the proximal quadrant 1811 and the distal quadrant 1813, respectively.

There are multiple ways in which the extending portions 1823 can be adapted to reduce the effects that the extensions have on the motion range of the hip joint.

Figure 10:
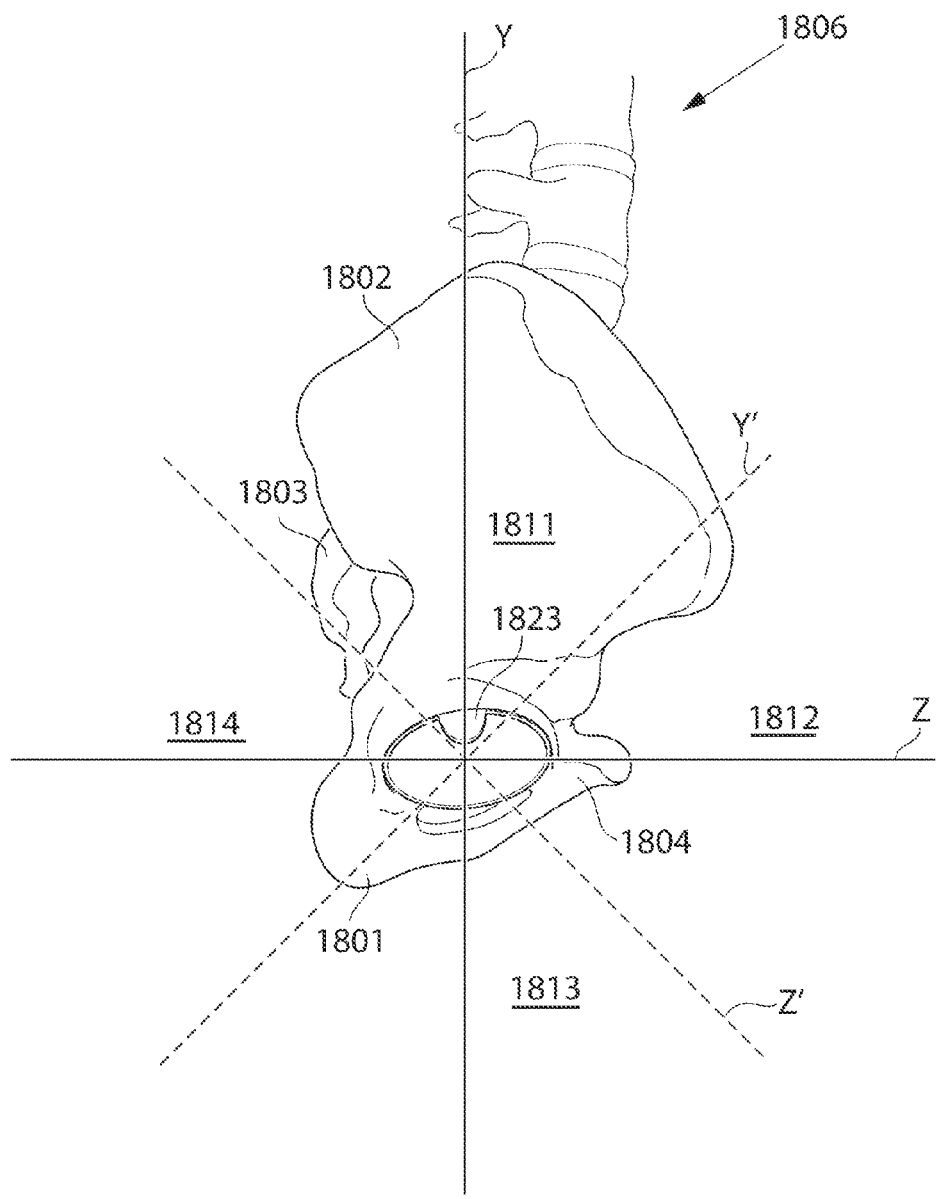
FIG. 10 shows pelvis in a lateral view, when the medical device is implanted.

FIG. 10 shows the pelvis in a lateral view, the medical device shown comprises one extending portion 1823 extending and being adapted to clasp the caput femur, or a prosthetic replacement therefor. The extending portion 1823 extends longitudinally along the equator line within the proximal quadrant 1811, which is further disclosed with reference to FIG. 3. According to the embodiment shown in FIG. 10, the extending portion 1823 extends in distal-lateral direction from the acetabulum.

Figure 11:
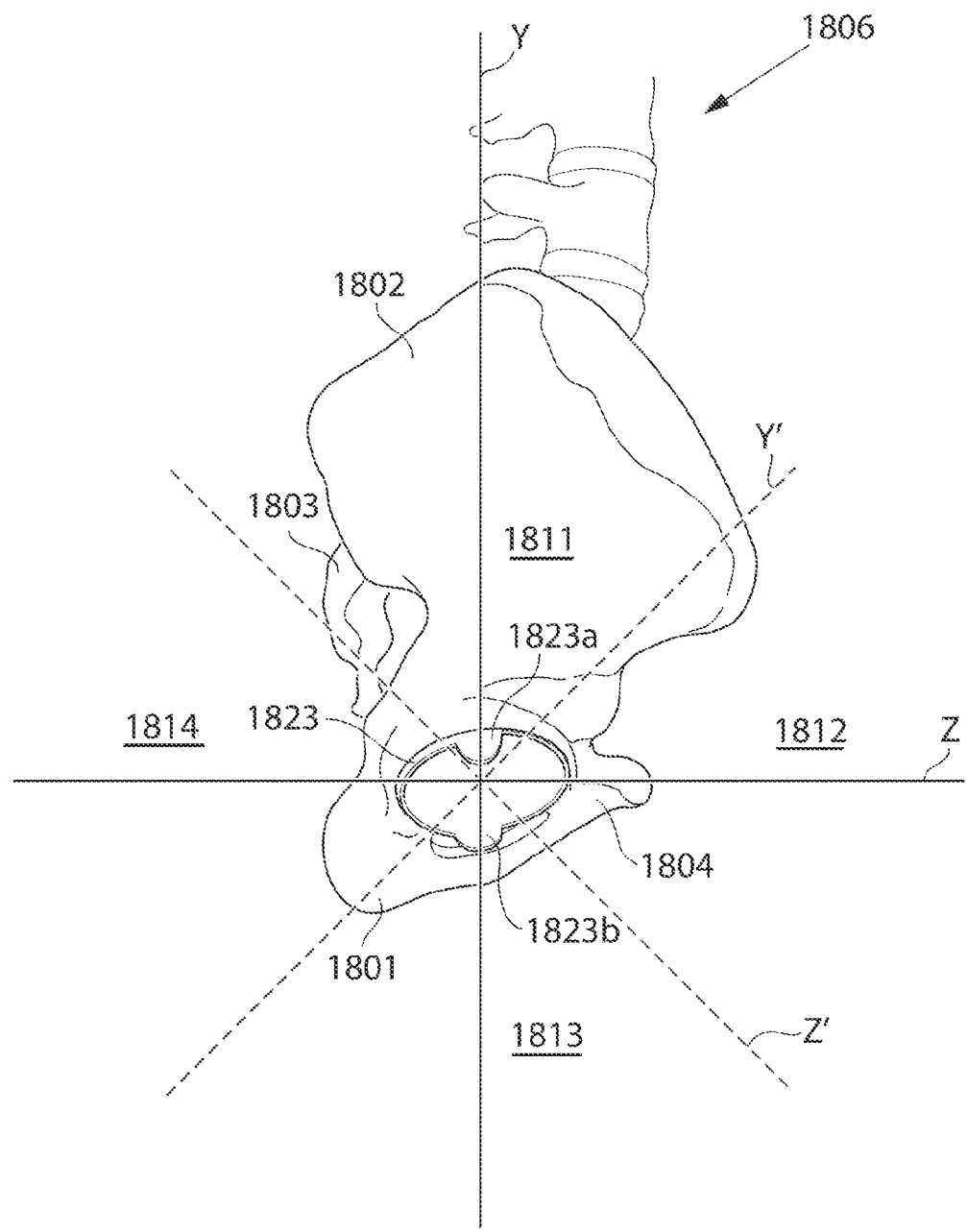
FIG. 11 shows pelvis in a lateral view, when the medical device is implanted.

FIG. 11 shows the pelvis in a lateral view, the medical device shown comprises a continuously extending portion 1823 with two extending portions 1823a and 1823b extending further in relation to the average extension of the extending portion. The entire extending portion is placed in the proximal, distal and dorsal quadrants and the extending portions 1823a,b extending further than the average extension of the extending portion 1823 extends in the proximal and distal quadrant.

Figure 12:
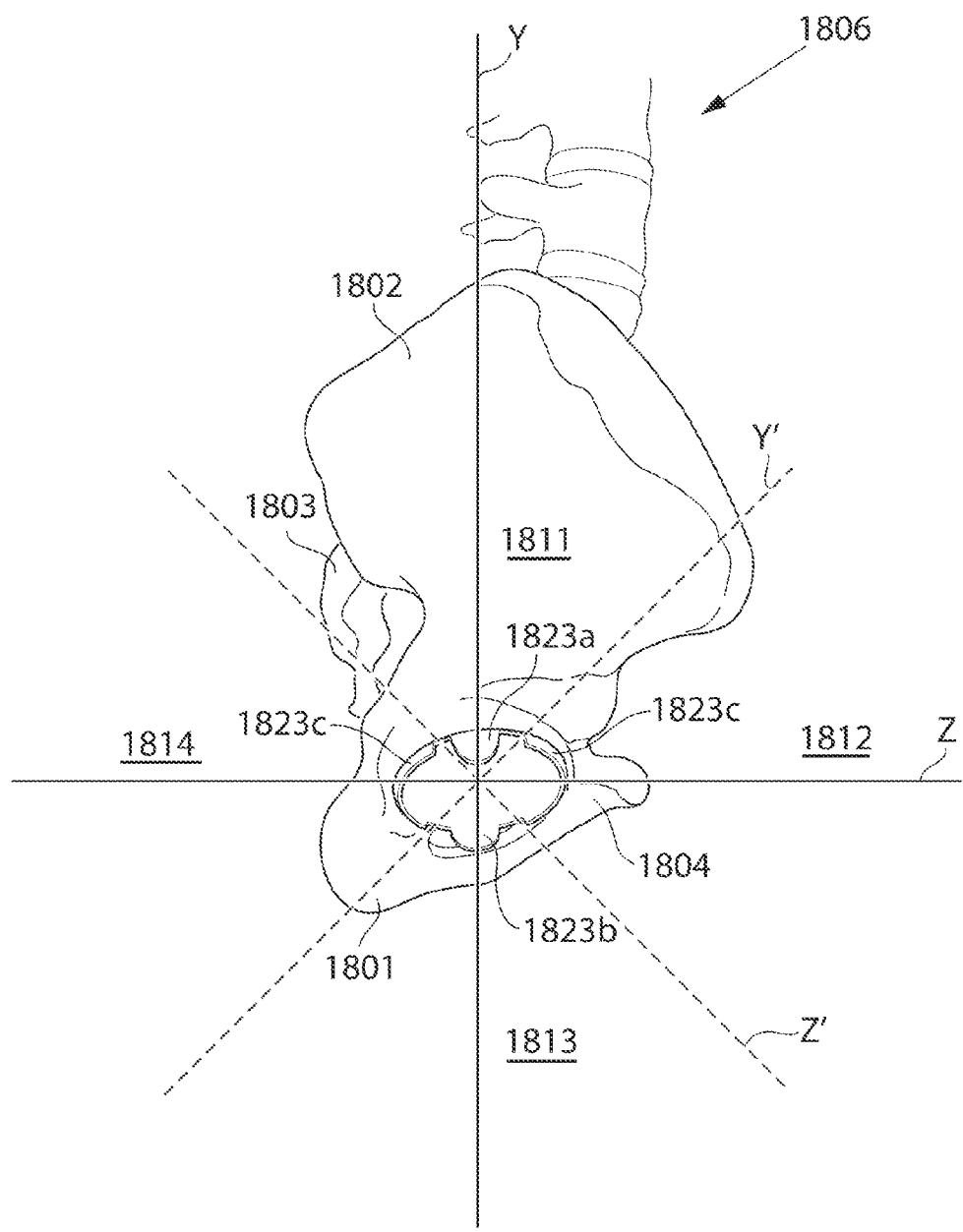
FIG. 12 shows pelvis in a lateral view, when the medical device is implanted.

FIG. 12 shows the pelvis in a lateral view, the medical device shown comprises four extending portions 1823a,b, c,d, wherein the first 1823a and second 1823b extending portions extends in the proximal and distal quadrant, respectively, thus the first extending portion 1823a extending in distal-lateral direction from the acetabulum, and the second extending portion 1823b extending medially towards foramen obturatum. The third extending portion 1823c extending in the frontal quadrant 1812, out from the acetabulum in dorsal direction, extends less than the first and second extending portion, since extending portions 1823c in the frontal quadrant is more limiting to the normal motion range of the hip joint. The fourth extending portion 1823d extends in the dorsal quadrant in accordance with the third extending portion 1823c do not extend as far as the first and second extending portions.

Figure 13:
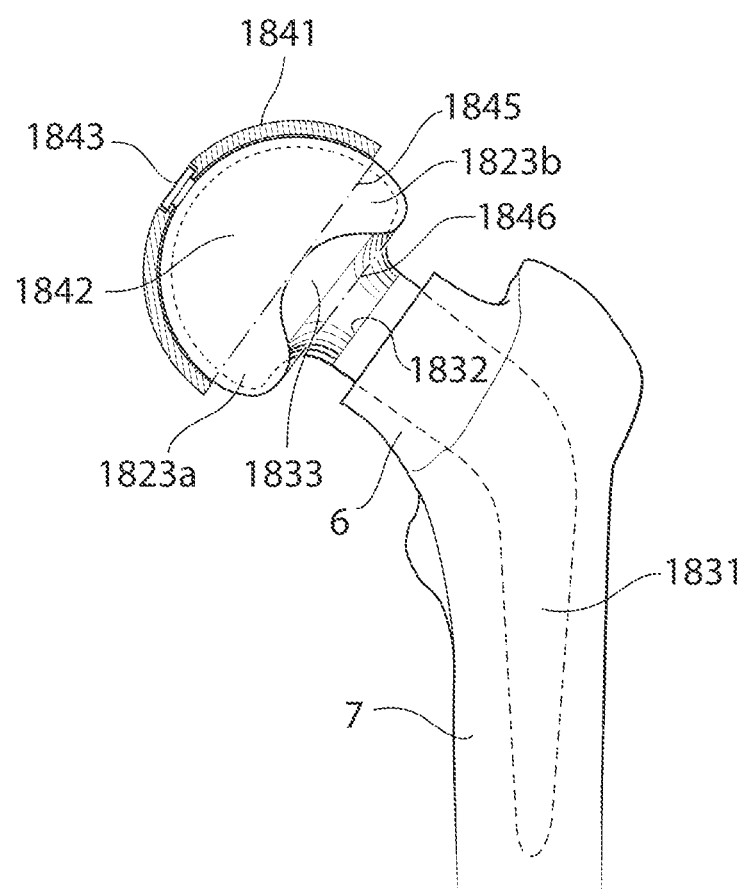
FIG. 13 shows the medical device according to yet another embodiment.

FIG. 13 shows an alternative embodiment of the medical device. In the alternative embodiment the medical device comprises a first part 1841 adapted to be fixated to the pelvic bone of the patient. The first part comprises an inner contacting surface adapted to be in movable connection with an outer contacting surface of a second part 1842. The second part 1842 is rotatably fixated to the first part 1841 by a rotatable connecting member 1843. An outer contacting surface of a prosthetic caput femur 1833 is adapted to be placed in contact with the inner surface of the second part 1842 and be movable in multiple directions, thus replicating the natural ball and socket joint of the hip. The second part 1842 comprises two extending portions 1823a,b extending beyond the equator line 1845 of the second part 1842. The extending portions 1823a,b extends longitudinally discontinuously along the equator line, thus creating an area between the extending portions, in which area a portion of the prosthetic collum femur can be placed, thus being placed partially between the equator line 1845 and the extension line 1846. The construction shown in FIG. 13 enables the second part 1842 to rotate if the collum femur 1832 engages the extending portions 1823a,b, which are sloped for this purpose. This way the second part 1842 are always placed such that the collum femur 1832 can be placed partially between equator line 1845 and the extension line 1846, which creates an optimal range of movement whilst the second part clasps the prosthetic caput femur 1833, and thus restricting the caput femur 1833 in the second part 1842 of the medical device. According to the embodiment shown the caput and collum femur is a prosthetic caput 1833 and collum 1832 femur, comprising a prosthetic stem 1831 adapted to be fixated in the femoral bone 7, however, in other embodiments, it is equally conceivable that the natural caput femur is resurfaced and placed in the second part 1842.

Figure 14A:
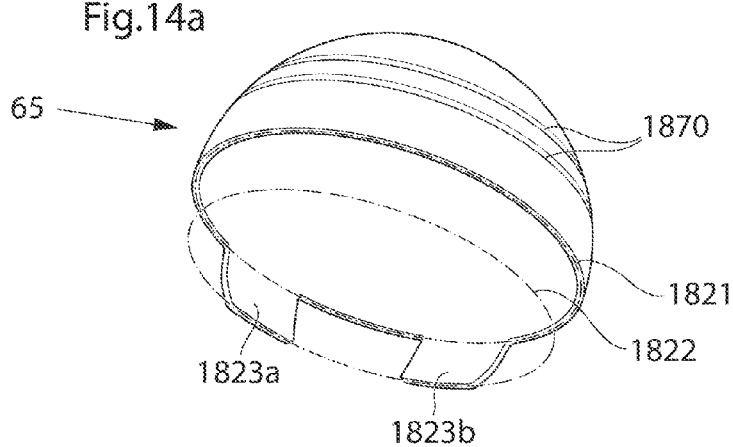
FIG. 14a shows the medical device according to one embodiment with two extending portions.

FIG. 14a shows the medical device 65 in a perspective view from below according to one embodiment. In this embodiment the medical device comprises two extending portions 1823a, b. The medical device 65 is according to this embodiment adapted to be fixated to the pelvic bone by means of an adhesive which is adapted to be placed in connection with the adhesive recesses 1870 of the outer surface of the medical device 65.

Figure 14B:
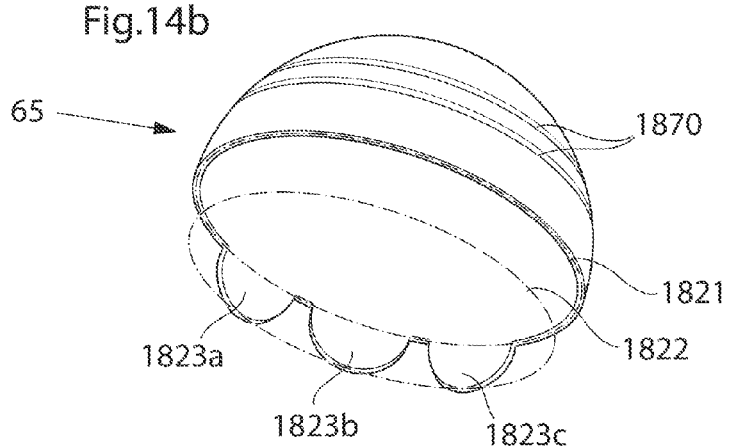
FIG. 14b shows the medical device according to one embodiment with three extending portions.

FIG. 14b shows a medical device similar to the medical device disclosed with reference to FIG. 14a, but with the difference that it comprises three equally extending portions 1823a,b,c.

Figure 14C:
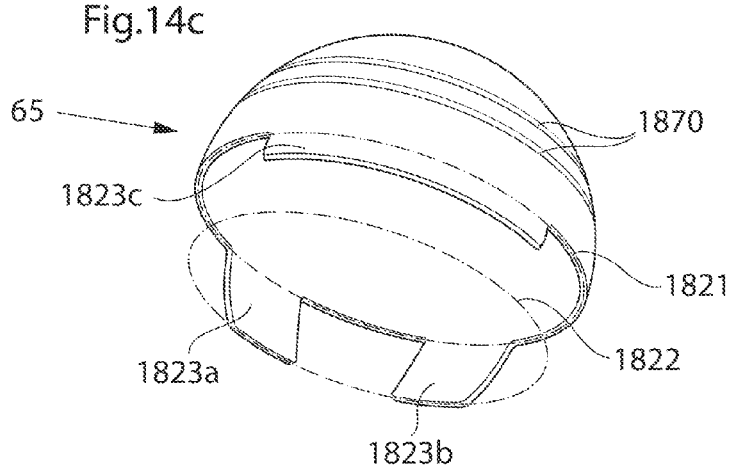
FIG. 14c shows the medical device according to one embodiment with three extending portions.
Figure 14D:
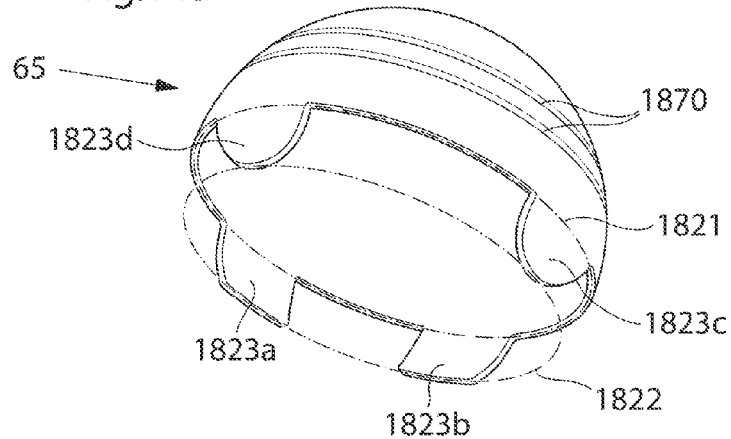
FIG. 14d shows the medical device according to one embodiment with four extending portions.
Figure 14E:
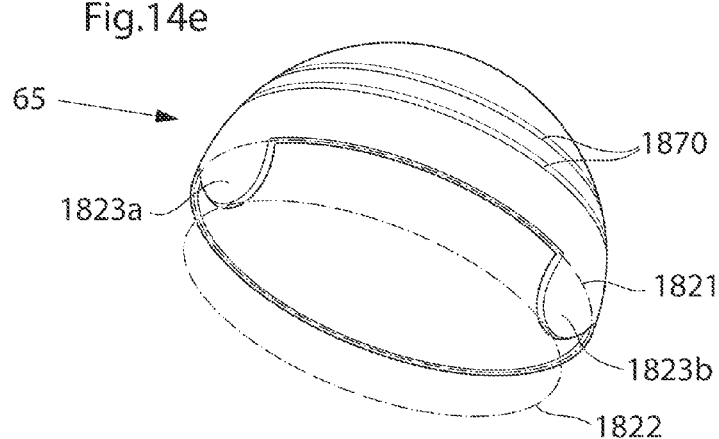
FIG. 14e shows the medical device according to one embodiment with two extending portions.
Figure 14F:
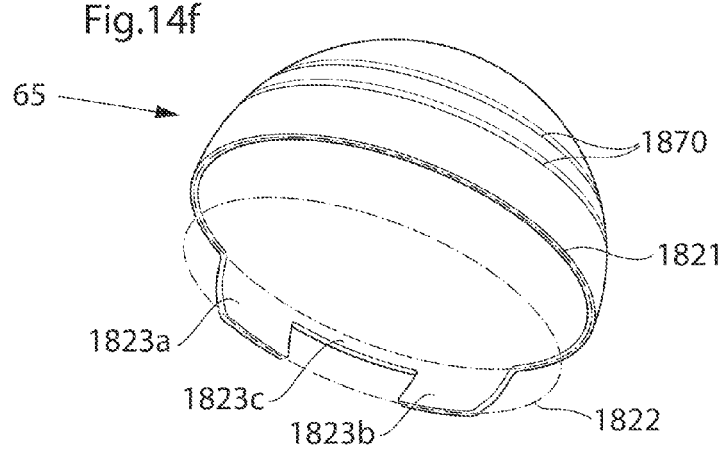
FIG. 14f shows the medical device according to one embodiment with three extending portions.

FIG. 14c shows a medical device similar to the medical device disclosed with reference to FIG. 14a, but with the difference that it comprises two equally extending portions 1823a,b and one less extending portion 1823c.

FIG. 14b shows a medical device similar to the medical device disclosed with reference to FIG. 14a, but with the difference that it comprises four equally extending portions 1823a,b,c,d.

FIG. 14b shows a medical device similar to the medical device disclosed with reference to FIG. 14a, but with the difference that the two extending portions are placed further from each other, and thus being adapted to be placed in the proximal and distal quadrant, when implanted.

FIG. 14b shows a medical device similar to the medical device disclosed with reference to FIG. 14a, but further comprising a less extending portion 1823c placed between the first and second extending portions 1823a,b.

The extending portions of the medical device which have been described could be made from an elastic material, enabling the extending portions to pass onto the caput femur.

Figure 15A:
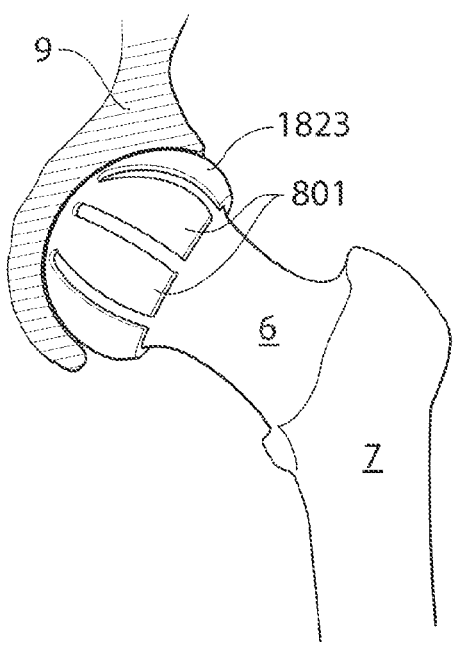
FIG. 15a shows the hip joint in section when a medical device is implanted, in its first state.

FIG. 15a shows the medical device in an embodiment in which the medical device is fixated to the pelvic bone 9. The medical device comprises extending portions which in turn serves as releasing members 801 adapted, in a first state, to hold the caput femur in the medical device and in a second state release the caput femur 5 from the medical device. The releasing member 801 is adapted to change from the first state to the second state when a pre-determined strain is placed on the releasing member 801. The strain could be caused by an abnormal movement of the hip joint, e.g. as the result of the patient falling. According to the embodiment shown in FIG. 14 the releasing member 801 comprises an elastic portion comprising elastic material, in the embodiment shown being the entire releasing member 801. The releasing member is adapted to non-invasively be able to change from the first state to the second state and from the second state to the first state, when a pre-determined strain is placed on the releasing member 801 i.e.

Figure 15B:
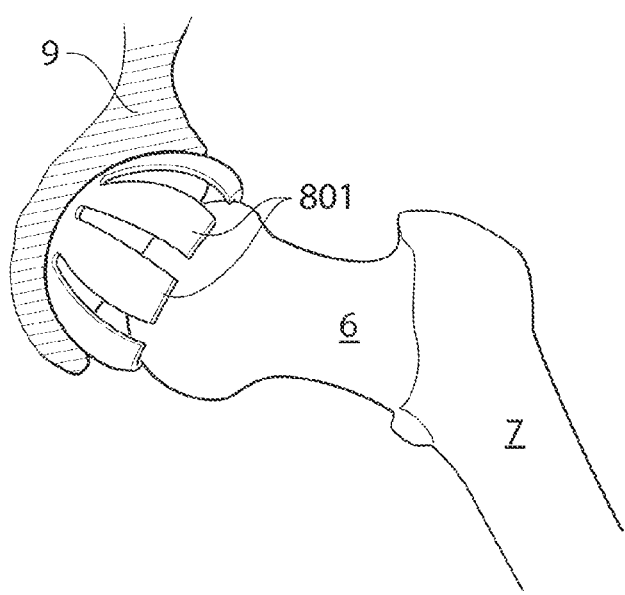
FIG. 15b shows the hip joint in section when a medical device is implanted, in its second state.

FIG. 15b shows the hip joint in section when the releasing member 801 is in its second state, wherein the releasing member 801 is adapted to release the caput femur 5 from the medical device placed in the pelvic bone 9. The releasing member 801 has changed from the first state to the second state because a pre-determined strain has been placed on the releasing member 801.

FIG. 16 shows the medical device according to an embodiment where the medical device comprises holding members 802a,b, adapted to slide against the caput femur 5, or a prosthetic replacement therefore. The holding members are adapted to, in a first state, hold the caput femur 5, or a prosthetic replacement therefore, in a second state the releasing member 801 is adapted to release the caput femur 5, or a prosthetic replacement therefore, from the medical device placed in the pelvic bone 9. The holding members 802a,b are spring loaded through a spring 803a,b being placed between a calibration member, being a calibration screw 804a,b, and the holding members 802a,b. The force exerted on the holding members 802a,b from the spring 803a,b is adapted to hold the caput femur 5, or a prosthetic replacement therefore, in the medical device in normal, functional hip joint movements, but release the caput femur 5, or a prosthetic replacement therefore, from the medical device when a pre-determined strain is placed on the releasing member which could be caused by an abnormal movement of the hip joint, e.g. as the result of the patient falling. The calibration screws 804a,b enables the pre-determination of the strain which will cause the holding members 802a,b to change from being in a first state to being in a second state.

FIG. 17 shows the releasing members in their second state, when a pre-determined strain has been exceeded, preferably being caused by an abnormal movement of the hip joint, e.g. as the result of the patient falling. The holding members 802a,b are retracted into sleeves 806 of the medical device, thereby compressing the springs 803a,b. The retraction of the holding members 802a,b causes the caput femur 5, or a prosthetic replacement therefore, to be dislocated/luxated from its position in the medical device, which, when large strain is placed on the hip joint and femoral bone 7, reduces the risk of the patient fracturing the femoral bone 7 or the pelvic bone 9. The holding members 802a,b are adapted to non-invasively be able to change from the first state to the second state and from the second state to the first state, when a pre-determined strain is placed on the holding members 802a,b.

FIG. 18 shows the medical device in section, with the holding members 802, placed in sleeves 806 evenly distributed along the cross-section of the medical device, holding the caput femur 5, or a prosthetic replacement therefore, in position in the medical device.

Figure 19:
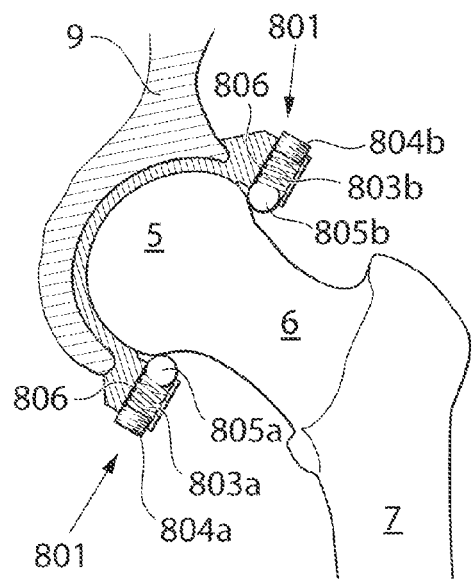
FIG. 19 shows the hip joint in section when a medical device is implanted, in its first state.

FIG. 19 shows an alternative embodiment of the principle shown in FIGS. 16-18, wherein the holding members 802a, b, comprises ball shaped members 805a,b in contact with the caput femur 5, or a prosthetic replacement therefore, and being adapted to roll against the caput femur 5, or a prosthetic replacement therefore, holding the caput femur 5, or a prosthetic replacement therefore, in place in the medical device, by the holding members 802a,b exerting force on the caput femur 5, or a prosthetic replacement therefore, through the contact with the springs 803a,b supported by the calibration screws 804a,b.

Figure 20:
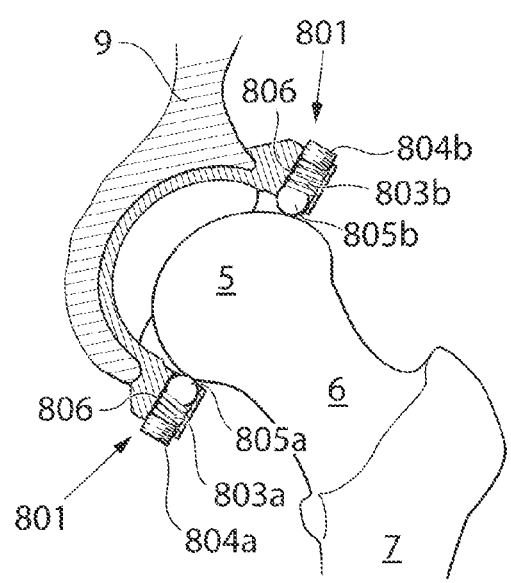
FIG. 20 shows the hip joint in section when a medical device is implanted, in its second state.

FIG. 20 shows the releasing members in their second state, when a pre-determined strain has been exceeded, preferably being caused by an abnormal movement of the hip joint, e.g. as the result of the patient falling. The holding members 802a,b, comprising the ball shaped members 805a, b, are retracted into sleeves 806 of the Medical device, thereby compressing the springs 803a,b. The retraction of the holding members 802a,b causes the caput femur 5, or a prosthetic replacement therefore, to be dislocated/luxated from its position in the medical device, which, when large strain is placed on the hip joint and femoral bone 7, reduces the risk of the patient fracturing the femoral bone 7 or the pelvic bone 9. The holding members 802a,b are adapted to non-invasively be able to change from the first state to the second state and from the second state to the first state, when a pre-determined strain is placed on the holding members 802a,b, which enables the caput femur 5, or a prosthetic replacement therefore, to be replaced in the medical device without a surgical procedure.

Figure 21:
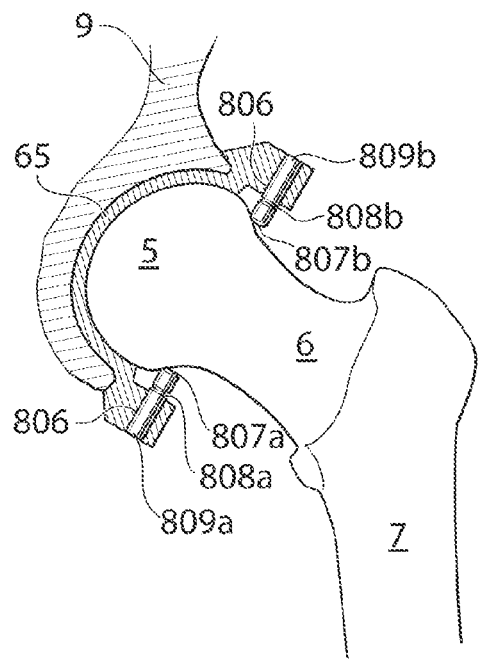
FIG. 21 shows the hip joint in section when a medical device is implanted, in its first state.

FIG. 21 shows the medical device in an embodiment wherein the releasing members 801 comprises a rupture device 807, 808, 809 adapted to fail at a pre-determined strain. According to this embodiment the rupture device is a rupture pin 807, 808, 809 comprising a base part 809a,b fixated to the medical device and a rupture part 807a,b attached to the base part 809a,b through a weakened section 808a,b, in which section the rupture part 807a,b is detached from the base part 809a,b when a predetermined strain is placed on the rupture device in contact with the caput femur 5, or a prosthetic replacement therefore.

Figure 22:
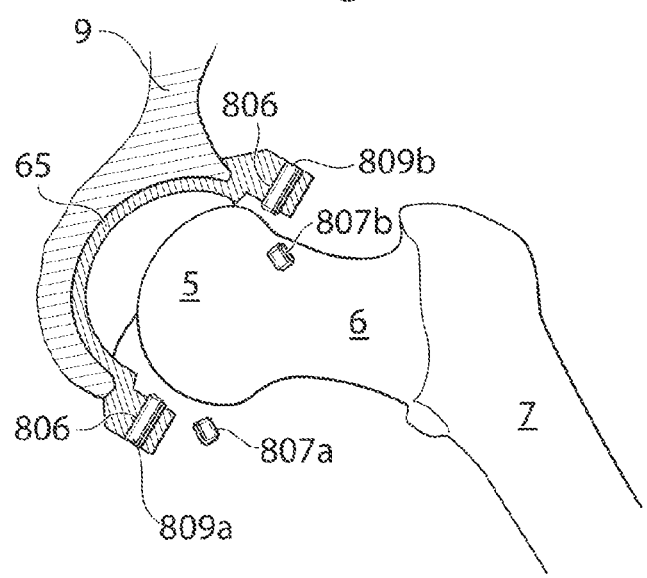
FIG. 22 shows the hip joint in section when a medical device is implanted, in its second state.

FIG. 22 shows the medical device according to the embodiment of FIG. 21 when the rupture device has failed due to a pre-determined strain on the rupture device being exceeded. According to one embodiment, (not shown) the rupture parts 807a,b are secured to the base part through a security wire keeping rupture parts 807a,b in proximity to the base part 809a,b even after the failure of the rupture device.

Figure 23A:
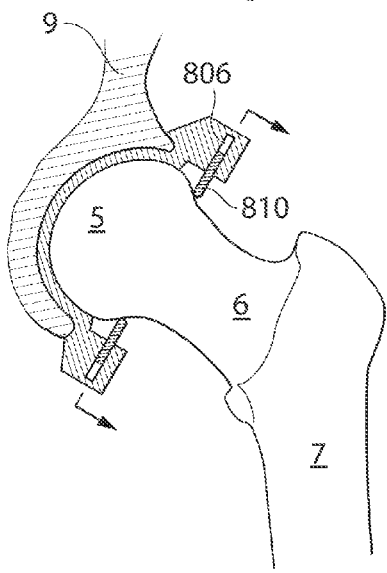
FIG. 23a shows the hip joint in section when a medical device is implanted, in its first state.

FIG. 23a shows the medical device according to an embodiment where the medical device comprises a circular sleeve 806, in which an elastic or rupture band 810 is provided. The elastic or rupture band 810 is adapted to at least partly encircle the ball shaped caput femur 5, or prosthetic replacement therefore. When a pre-determined strain is placed on the elastic or rupture band 810 the circular opening encircling the caput femur 5, or a prosthetic replacement therefore, is expanded and the caput femur 5, or a prosthetic replacement therefore, is released from the medical device, to which it is held by means of the elastic band 610. In embodiments where the medical device comprises a rupture band 810 holding the caput femur 5, or a prosthetic replacement therefore, in the medical device, a weakened portion 811 of the band 810 fails and thus the circular opening encircling the caput femur 5, or a prosthetic replacement therefore, is expanded and the caput femur 5, or a prosthetic replacement therefore, is released from the medical device. In the embodiments where the band 810 is an elastic band 810 it is conceivable that the band 810 comprises an elastic part or section, or that the entire band 810 is made of an elastic material.

Figure 23B:
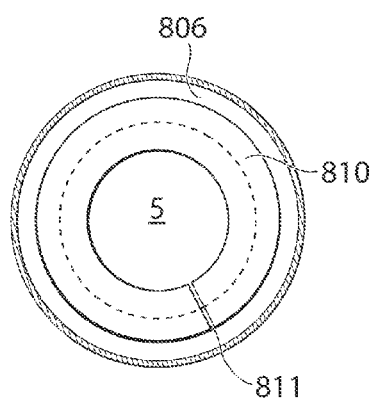
FIG. 23b shows a medical device in section when in its first state.

FIG. 23b shows the medical device in section when the elastic or rupturing band 810, holding the caput femur 5, or a prosthetic replacement therefore, is placed in a circular sleeve 806 in the medical device. An opening or weakened portion 811 is provided perpendicular to the circumference of the band 810.

Figure 24A:
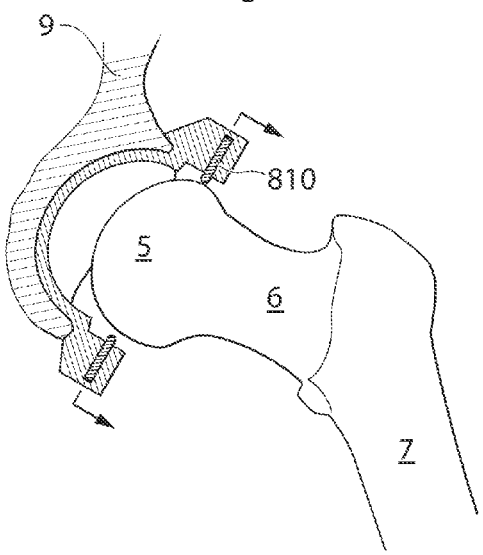
FIG. 24a shows the hip joint in section when a medical device is implanted, in its second state.
Figure 24B:
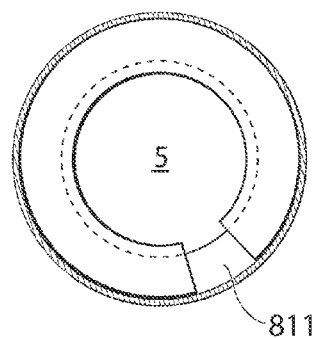
FIG. 24b shows a medical device in section when in its second state.

FIG. 24a shows the medical device in a second state where the caput femur 5, or a prosthetic replacement therefore, is released from the connection with the medical device, after a pre-determined stain has been placed on the elastic or rupture band 810. As shown in FIG. 24b, the gap or weakened part has been expanded, thereby allowing the caput femur, or a prosthetic replacement therefore, 5 to pass through the opening defined by the elastic or rupture band 810. The medical device could be adapted to non-invasively be able to change from the first state to the second state and from the second state to the first state, when a pre-determined strain is placed on the band 810, which enables the caput femur 5, or a prosthetic replacement therefore, to be replaced in the medical device without a surgical procedure.

Figure 25:
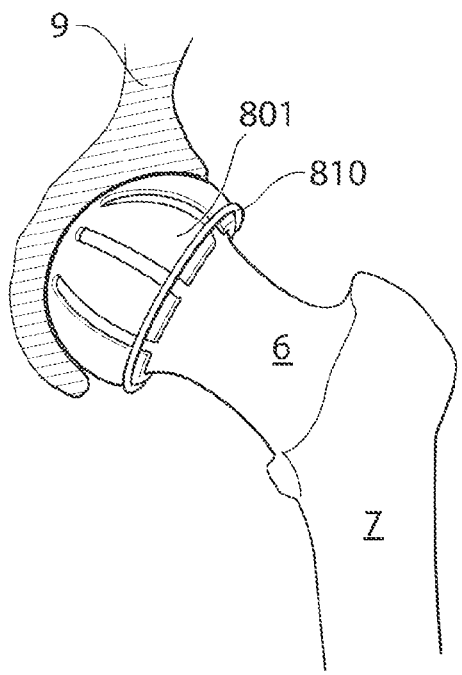
FIG. 25 shows the hip joint in section when a medical device is implanted, in its first state.

FIG. 25 shows the medical device according to an embodiment where the releasing member 801 comprises an elastic wing of the medical device, which is assisted by an elastic or rupture band 810 encircling the medical device by enclosing the caput femur 5, or a prosthetic replacement therefore, in the medical device passing beyond the point of the caput femur 5, or a prosthetic replacement therefore, having a largest cross-sectional distance. The elastic or rupture band 810 is held in place to the medical device by means of the band 810 being placed in a groove along the circumference of the medical device. However, said groove could be assisted or replaced by an adhesive or a mechanical fixation element.

Figure 26:
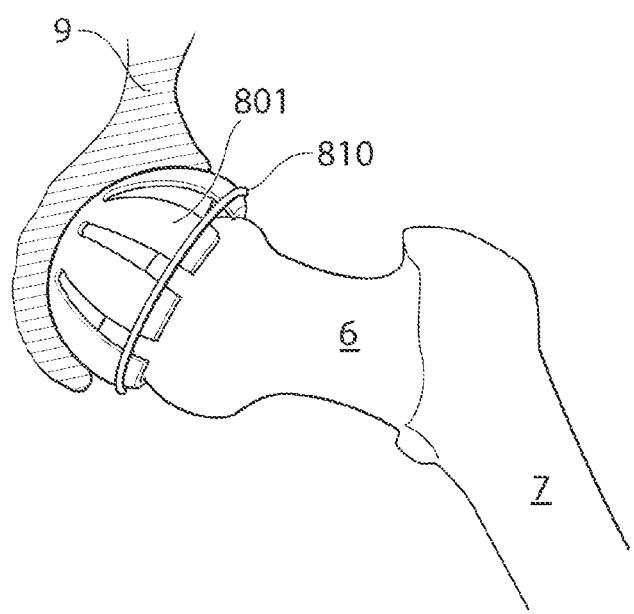
FIG. 26 shows the hip joint in section when a medical device is implanted, in its second state.

FIG. 26 shows the medical device when in its second state, in which the releasing member 801 releases the caput femur 5 or a prosthetic replacement therefore, from the medical device. In embodiments when the band 810 is an elastic band 810 it could be expanded, thereby enlarging the hole through which the caput femur 5, or a prosthetic replacement therefore, can pass. In embodiments where the band 810 is a rupture band, the band 810 fails and thereby the caput femur 5, or a prosthetic replacement therefore, is held in place solely by the releasing member 801 which is a part of the extending portion adapted to release the caput femur 5, or a prosthetic replacement therefore, at a pre-defined strain. The medical device could be adapted to non-invasively be able to change from the first state to the second state and from the second state to the first state, when a pre-determined strain is placed on the band 810 and/or the releasing member 801, which enables the caput femur 5, or a prosthetic replacement therefore, to be replaced in the medical device without a surgical procedure.

Figure 27:
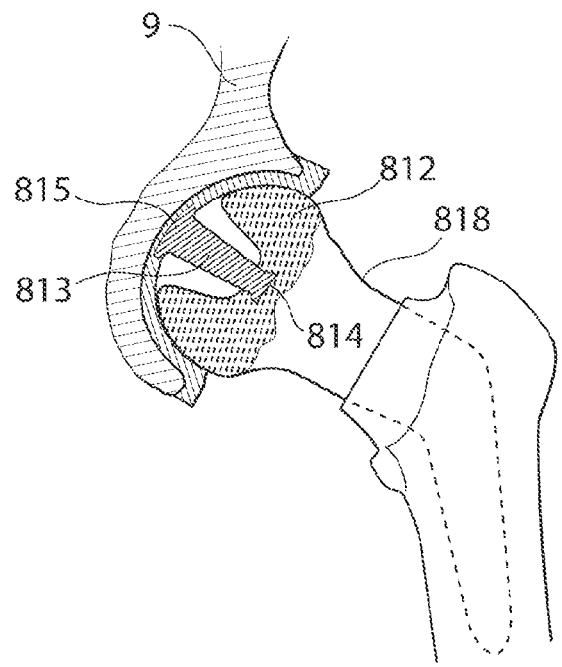
FIG. 27 shows the hip joint in section when a medical device is implanted, in its first state.

FIG. 27 shows the hip joint in section according to an embodiment where the caput femur 5, or a prosthetic replacement therefore, and collum femur 6 have been replaced with a prosthetic part 818 fixated to the femoral bone 7, either with bone cement, or without. The prosthetic part 818 comprises a prosthetic caput femur 812 having a cavity 816 in which a rupture band 813 fixated to a fixation portion 814 of the prosthetic caput femur 812, and a fixating portion 815 of the medical device. The cavity 816 is adapted to enable the prosthetic caput femur 812 to perform normal functional hip movements inside the medical device. The rupture band 813 is adapted to hold the prosthetic caput femur 812 to the medical device in a first state, and release the prosthetic caput femur 812 from the medical device when a pre-determined strain is placed on the rupture band 813.

Figure 28:
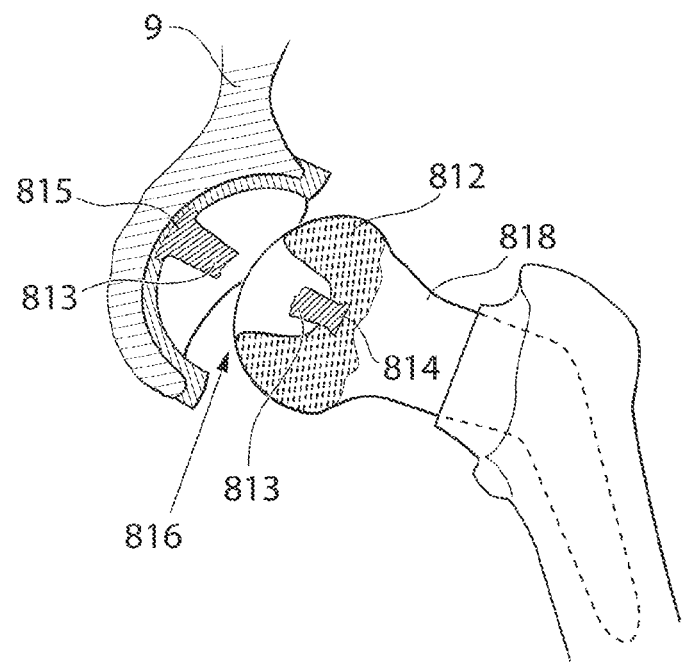
FIG. 28 shows the hip joint in section when a medical device is implanted, in its second state.

FIG. 28 shows the embodiment of the medical device according to FIG. 27, in a second state in which the rupture band 813 has failed and thereby the prosthetic caput femur 812 is released from the medical device. The rupture band 813 could be fixated to a fixation portion 814 of the prosthetic caput femur 812, and/or a fixating portion 815 of the medical device using: at least one screw, at least one pin, form fitting, welding, adhesive, pin, wire, a ball mounted into a bowl, a male portion of one part mounted into a female portion of the other part, a key introduced into a lock being portions of said parts, band, or other mechanical connecting members. The failing of the rupture band 813 is which could be caused by an abnormal movement of the hip joint, e.g. as the result of the patient falling.

Figure 29:
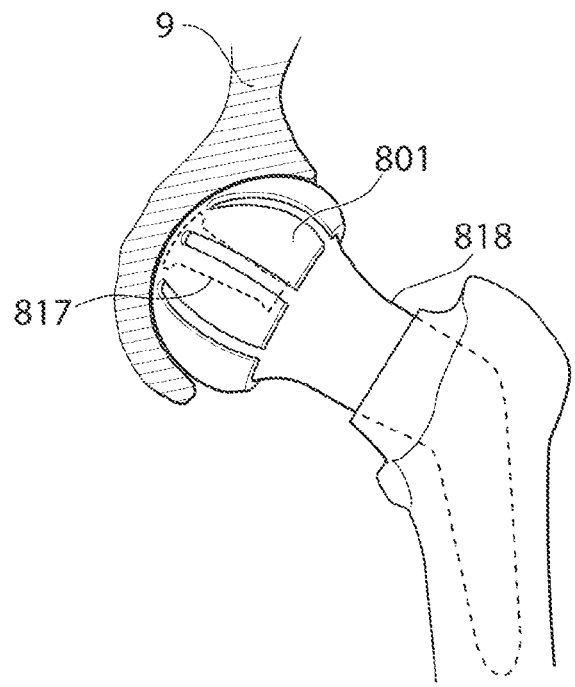
FIG. 29 shows the hip joint in section when a medical device is implanted, in its first state.

FIG. 29 shows a prosthetic part 818 according to an embodiment where the prosthetic part 818 is fixated to the femoral bone 7 and comprises a caput femur 812 comprising a cavity 816 adapted to enable the hip joint to perform functional hip joint movements while in a first state held to the medical device using an elastic bend 817 fixated to a fixation portion 814 of the prosthetic caput femur 812, and a fixating portion 815 of the medical device, and a releasing member 801 according to the embodiment shown in FIGS. 9 and 10. The combination of the releasing member 801 and the elastic band 817 is adapted to, in a first state hold the prosthetic part 818 to the medical device, and in a second state release the prosthetic part 818 from the medical device. According to another embodiment (not shown) the prosthetic part is held to the medical device solely using the elastic band 817, of course also supported by the remainder of the hip joint capsule and the affected muscles. FIG. 29 shows a prosthetic caput femur 812 and a prosthetic acetabulum comprising the releasing member 801. A totally prosthetic embodiment is conceivable with regards to all of the embodiments of the releasing members disclosed herein. In any of these embodiments i.e. in embodiments where both the caput femur and the acetabulum are prosthetic parts, the prosthetic caput femur and prosthetic acetabulum could be pre-mounted when implanted in a patient such that one unit is implanted in the patient comprising the functioning hip joint.

Figure 30:
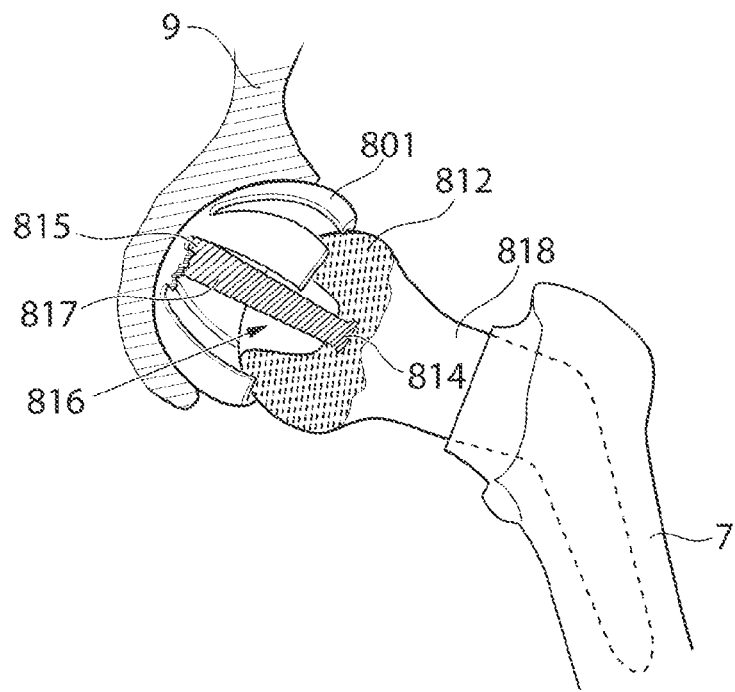
FIG. 30 shows the hip joint in section when a medical device is implanted, in its second state.

FIG. 30 shows the embodiment of the medical device according to FIG. 29, in a second state in which the elastic band 817 is stretched such that the prosthetic part 818 is released from the medical device. The elastic band 817 could be fixated to a fixation portion 814 of the prosthetic caput femur 812, and/or a fixating portion 815 of the medical device using: at least one screw, at least one pin, form fitting, welding, adhesive, pin, wire, a ball mounted into a bowl, a male portion of one part mounted into a female portion of the other part, a key introduced into a lock being portions of said parts, band, or other mechanical connecting members. The failing of the rupture band 813 is preferably caused by an abnormal movement of the hip joint, e.g. as the result of the patient falling. The elastic band 817 could comprise an elastic part or section, which could be the entire elastic band 818, made from an elastic material, such as an elastic polymer material such as: a copolymer material such as polystyrene, poly(ethylene-butylene) or polystyrene. It is also conceivable that the material is a polyurethane elastomeric material, polyamide elastomeric materials and polyester elastomeric materials elastic copolymers of ethylene and at least one vinyl monomer such as, for example, vinyl acetates, unsaturated aliphatic monocarboxylic acids, and esters of such monocarboxylic acids. The elastic band 813 could comprise a barrier coating, which cannot be penetrated by body cells. Preferably, the barrier coating comprises a Parylene™ coating, or a biocompatible metal coating, such as gold, silver or titanium. According to other embodiments the elastic band comprises a spring type member, a combination of metal and plastic materials, a combination of metal and carbon based material or a combination of carbon and plastic based material.

Figure 31:
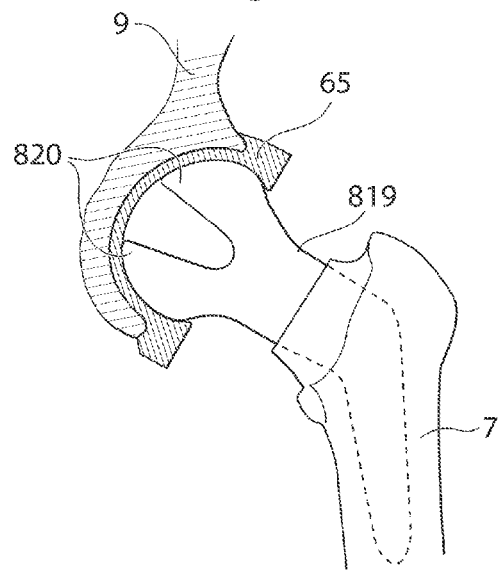
FIG. 31 shows the hip joint in section when a medical device is implanted, in its first state.

FIG. 31 shows the hip joint in section in an embodiment where the medical device comprises a prosthetic part 819 adapted to be fixated to the femoral bone 7. The prosthetic part comprises a prosthetic caput femur which is adapted to comprise elastic elements 820 which act as a releasing member holding the prosthetic caput femur inside of the medical device fixated to the pelvic bone. The elastic elements 820 of the prosthetic caput femur, is preferably made of an elastic material, which for example could be an elastomeric polymer material or an elastic metal material. It is conceivable that the elastic material comprises an outer layer in connection with the medical device which is adapted to resist the wear from the contact with the medical device. The elastic element is adapted to compress when a pre-determined strain is placed on the hip joint and thereby on the elastic elements 820. When the elastic elements 820 are compressed the prosthetic caput femur is released from the medical device.

Figure 32:
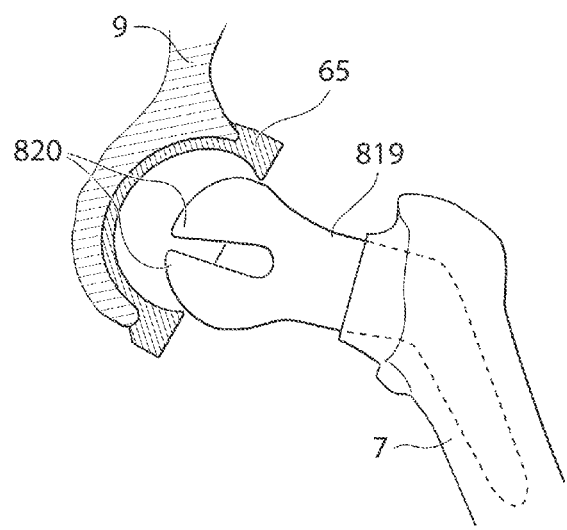
FIG. 32 shows the hip joint in section when a medical device is implanted, in its second state.

FIG. 32 shows the medical device according to the embodiment shown in FIG. 31, in a second state, in which the elastic element 820 has been compressed, following a pre-determined strain being placed on the medical device. The medical device is thereby placed in a second state, in which the prosthetic caput femur is released from the medical device, wherein it has been held.

Figure 33:
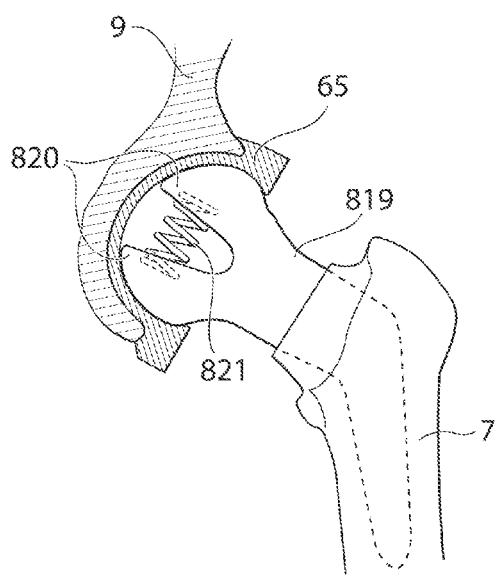
FIG. 33 shows the hip joint in section when a medical device is implanted, in its first state.

FIG. 33 shows an embodiment of the medical device in which the elastic elements 820 are further assisted by a spring 821 in connection with two elastic elements 820, the spring 821 is compressed alongside the elastic members 820, when a pre-determined strain is placed on the prosthetic part 819 comprising the prosthetic caput femur.

Figure 34:
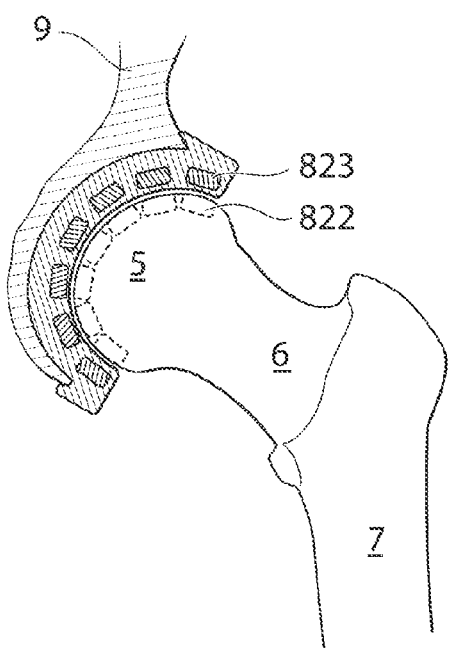
FIG. 34 shows the hip joint in section when a medical device is implanted, in its first state.

FIG. 34 shows the hip joint in section when a medical device for, in a first state, holding the caput femur 5, or a prosthetic replacement therefore, to the medical device, and in a second state releasing the caput femur 5, or a prosthetic replacement therefore from the medical device. The medical device is adapted to change from being in the first state to being in the second state at a pre-determined strain affecting the medical device by the connection with the pelvic bone 9 and the femoral bone 7, which reduced the risk of the patient fracturing the femoral bone 7 and/or the pelvic bone 9. The medical device comprises magnets 823 or magnetic material 823 placed in the medical device, and magnets 822 or magnetic material 822 placed in the caput femur 5 or a prosthetic replacement therefore. According to one embodiment a magnet 823 is placed in the medical device its south pole directed towards the caput femur 5, or prosthetic replacement therefore, and a magnet 822 placed in the caput femur 5, or prosthetic replacement therefore, having its north pole directed towards the medical device. However only one of the sides needs to be magnetic whereas the other side merely needs to comprise magnetic material. Any combination of north and south ends and magnets/magnetic material is hence conceivable. The magnetic force described is adapted to hold the caput femur 5, or a prosthetic replacement therefore, in the medical device in normal use, enabling the hip joint to perform functional hip joint movements, and release the caput femur 5, or a prosthetic replacement therefore, from the medical device when a predetermined strain is exceeded.

Figure 35:
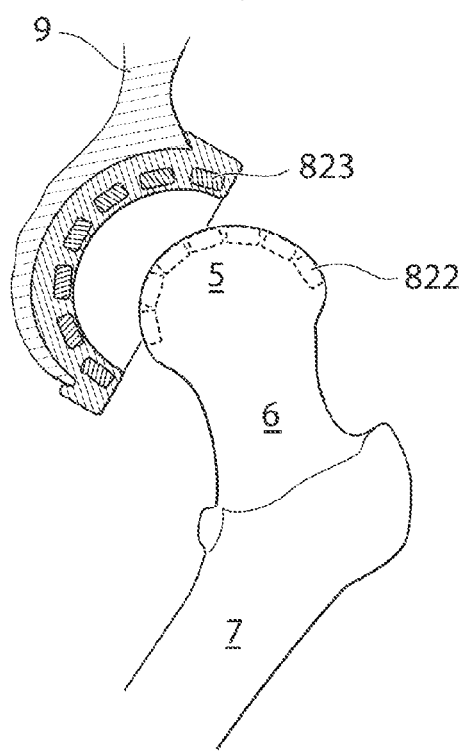
FIG. 35 shows the hip joint in section when a medical device is implanted, in its second state.

FIG. 35 shows the medical device according to the embodiment of FIG. 30 in the second state, in which the caput femur 5, or a prosthetic replacement therefore, is released from the medical device as a result of a pre-determined level of strain being exceeded.

The medical device according to any of the embodiments could comprise at least one material selected from a group consisting of: polytetrafluoroethylene (PTFE), perfluoro-alkoxy (PFA) and fluorinated ethylene propylene (FEP). It is furthermore conceivable that the material comprises a metal alloy, such as cobalt-chromium-molybdenum or titanium or stainless steel, or polyethylene, such as cross-linked polyethylene or gas sterilized polyethylene. The use of ceramic material is also conceivable, in the contacting surfaces or the entire medical device such as zirconium or zirconium dioxide ceramics or alumina ceramics. The part of the medical device in contact with human bone for fixation of the medical device to human bone could comprise a poorhouse structure which could be a porous micro or nano-structure adapted to promote the growth-in of human bone in the medical device for fixating the medical device. The porous structure could be achieved by applying a hydroxy-apatite (HA) coating, or a rough open-pored titanium coating, which could be produced by air plasma spraying, a combination comprising a rough open-pored titanium coating and a HA top layer is also conceivable. The contacting parts could be made of a self lubricated material such as a waxy polymer, such as PTFE, PFA, FEP, PE and UHMWPE, or a powder metallurgy material which could be infused with a lubricant, which preferably is a biocompatible lubricant such as a Hyaluronic acid derivate. It is also conceivable that the material of contacting parts or surfaces of the medical device herein is adapted to be constantly or intermittently lubricated. According to some embodiments the parts or portions of the medical device could comprise a combination of metal materials and/or carbon fibers and/or boron, a combination of metal and plastic materials, a combination of metal and carbon based material, a combination of carbon and plastic based material, a combination of flexible and stiff materials, a combination of elastic and less elastic materials, Corian or acrylic polymers.

Please note that any embodiment or part of embodiment as well as any method or part of method could be combined in any way. All examples herein should be seen as part of the general description and therefore possible to combine in any way in general terms.

The invention claimed is:

1. A medical device for implantation in a hip joint of a patient, wherein said medical device is adapted to be fixated to a pelvic bone of the patient, and wherein said medical device comprises an inner and an outer surface, wherein a contacting portion of said inner surface is spherical and adapted to face a centre of the hip joint when said medical device is implanted, and wherein said medical device is adapted to receive a caput femur or a prosthetic caput femur having a spherical portion, wherein
   a) said medical device comprises at least one extending portion adapted to clasp the caput femur, or prosthetic caput femur, for restraining said caput femur, or said prosthetic caput femur in said medical device,
   b) said at least one extending portion comprises an elastic portion, and wherein
   c) said medical device is adapted to release the caput femur or prosthetic caput femur from said medical device by deflecting said at least extending portion when a predetermined strain is placed on said medical device by abnormal movement of the hip joint caused by the patient.

2. The medical device according to claim 1, wherein said medical device is adapted to receive a caput femur or an artificial replacement therefor having a collum femur or artificial collum femur fixated to said spherical portion of said caput femur or artificial replacement therefor, wherein:
   a) said inner surface comprises an equator line, being the largest circular circumference of said inner surface,
   b) said at least one extending portion passes beyond said equator line, such that the end portion of said contacting portion of said inner surface forms a circular extension line having a smaller circumference than said equator line, and
   c) said at least one extending portion longitudinally extends discontinuously along said equator line, such that a portion of said collum femur or prosthetic collum femur can be placed between said extension line and said equator line.

3. The medical device according to claim 2, wherein said extension line is placed distal to the equator line, when the medical device is implanted.

4. The medical device according to claim 1, wherein said elastic portion comprises an elastic material.

5. The medical device according to claim 1, wherein said elastic portion is further supported by an elastic band.

6. The medical device according to claim 5, wherein said elastic band is adapted to at least partly encircle the caput femur.

7. The medical device according to claim 1, wherein said at least one extending portion is adapted to slide against the caput femur.

8. The medical device according to claim 1, wherein said medical device comprises a second extending portion adapted to clasp the caput femur, or prosthetic caput femur, for restraining said caput femur, or said prosthetic caput femur in said medical device.

9. The medical device according to claim 8, wherein said medical device's extending portion and second extending portion together define an intermediate void adapted to receive an outer portion of a collum femur or a prosthetic collum femur when the collum femur or prosthetic collum femur is moved from its neutral position towards said void.

10. The medical device according to claim 8, wherein said medical device comprises a third extending portion adapted to clasp the caput femur, or prosthetic caput femur, for restraining said caput femur, or said prosthetic caput femur in said medical device.

11. The medical device according to claim 10, wherein said medical device's second extending portion and third extending portion together define an intermediate void adapted to receive an outer portion of a collum femur or a prosthetic collum femur when the collum femur or prosthetic collum femur is moved from its neutral position towards said void.

12. The medical device according to claim 11, wherein said medical device comprises a fourth extending portion adapted to clasp the caput femur, or prosthetic caput femur, for restraining said caput femur, or said prosthetic caput femur in said medical device.

* * * * *